United States Patent
Goldberg et al.

(10) Patent No.: US 9,593,934 B2
(45) Date of Patent: Mar. 14, 2017

(54) INTEGRATED DUAL SWEPT SOURCE FOR OCT MEDICAL IMAGING

(71) Applicant: Axsun Technologies, Inc., Billerica, MA (US)

(72) Inventors: Brian Goldberg, Cambridge, MA (US); Dale C. Flanders, Lexington, MA (US); Walid A. Atia, Lexington, MA (US); Bartley C. Johnson, North Andover, MA (US); Mark E. Kuznetsov, Lexington, MA (US)

(73) Assignee: Axsun Technologies LLC, Billerica, MA (US)

( * ) Notice: Subject to any disclaimer, the term of this patent is extended or adjusted under 35 U.S.C. 154(b) by 0 days.

(21) Appl. No.: 14/175,158

(22) Filed: Feb. 7, 2014

(65) Prior Publication Data

US 2014/0152997 A1    Jun. 5, 2014

Related U.S. Application Data

(62) Division of application No. 12/980,144, filed on Dec. 28, 2010, now Pat. No. 8,687,666.

(51) Int. Cl.
*G01B 9/02* (2006.01)
*G01N 21/47* (2006.01)
(Continued)

(52) U.S. Cl.
CPC ........ *G01B 9/02091* (2013.01); *A61B 5/0066* (2013.01); *G01N 21/4795* (2013.01);
(Continued)

(58) Field of Classification Search
CPC .............. G01B 9/0209; G01B 9/02091; G01B 9/02004; G01B 9/02007; H01S 3/10015
(Continued)

(56) References Cited

U.S. PATENT DOCUMENTS 5,202,745 A    4/1993 Sorin et al.
5,459,570 A    10/1995 Swanson et al.
(Continued)

OTHER PUBLICATIONS

Aguirre, A., et al., "Continuum generation in a novel photonic crystal fiber for ultrahigh resolution optical coherence tomography at 800 nm and 1300 nm," Optics Express, vol. 14, No. 3, Feb. 6, 2006, pp. 1145-1160.
(Continued)

*Primary Examiner* — Jonathan Hansen
(74) *Attorney, Agent, or Firm* — HoustonHogle LLP

(57) ABSTRACT

An optical coherence analysis system comprising: a first swept source that generates a first optical signal that is tuned over a first spectral scan band, a second swept source that generates a second optical signal that is tuned over a second spectral scan band, a combiner for combining the first optical signal and the second optical signal for form a combined optical signal, an interferometer for dividing the combined optical signal between a reference arm leading to a reference reflector and a sample arm leading to a sample, and a detector system for detecting an interference signal generated from the combined optical signal from the reference arm and from the sample arm. In embodiments, the swept sources are tunable lasers that have shared laser cavities.

14 Claims, 19 Drawing Sheets

(51) Int. Cl.
*H01S 5/14* (2006.01)
*A61B 5/00* (2006.01)
*H01S 5/022* (2006.01)
*H01S 5/40* (2006.01)

(52) U.S. Cl.
CPC ............ *H01S 5/141* (2013.01); *A61B 5/0075* (2013.01); *H01S 5/02216* (2013.01); *H01S 5/02248* (2013.01); *H01S 5/02284* (2013.01); *H01S 5/4012* (2013.01); *H01S 5/4062* (2013.01); *H01S 5/4068* (2013.01)

(58) Field of Classification Search
USPC ................................................. 356/479, 497
See application file for complete search history.

(56) References Cited

U.S. PATENT DOCUMENTS

| | | | |
|---|---|---|---|
| 6,256,102 B1 | 7/2001 | Dogariu | |
| 6,373,632 B1 | 4/2002 | Flanders | |
| 6,538,817 B1 | 3/2003 | Farmer et al. | |
| 6,570,659 B2 | 5/2003 | Schmitt | |
| 6,608,711 B2 | 8/2003 | Flanders et al. | |
| 7,061,618 B2 | 6/2006 | Atia et al. | |
| 7,391,520 B2 | 6/2008 | Zhou et al. | |
| 7,415,049 B2 | 8/2008 | Flanders et al. | |
| 7,538,884 B2 | 5/2009 | Teramura et al. | |
| 7,545,504 B2 | 6/2009 | Buckland et al. | |
| 7,554,668 B2 | 6/2009 | Zhou et al. | |
| 7,570,364 B2* | 8/2009 | Kuroiwa ............ G01N 21/4795 356/479 | |
| 7,573,021 B2 | 8/2009 | Haber et al. | |
| 7,852,484 B2 | 12/2010 | Teramura | |
| 8,139,226 B2* | 3/2012 | Johnson ........................ 356/477 | |
| 8,665,450 B2* | 3/2014 | Johnson et al. ............. 356/497 | |
| 2004/0064022 A1 | 4/2004 | Korn | |
| 2007/0002327 A1 | 1/2007 | Zhou et al. | |
| 2007/0291801 A1 | 12/2007 | Caprara et al. | |
| 2008/0031410 A1 | 2/2008 | Shimizu et al. | |
| 2008/0140325 A1 | 6/2008 | Teramura | |
| 2008/0165366 A1* | 7/2008 | Schmitt ................ A61B 5/0066 356/519 | |
| 2008/0175465 A1* | 7/2008 | Jiang et al. .................... 382/131 | |
| 2009/0059970 A1* | 3/2009 | Atia .................... G01N 21/4795 372/20 | |
| 2009/0284749 A1* | 11/2009 | Johnson ............... A61B 5/0066 356/497 | |
| 2009/0290167 A1* | 11/2009 | Flanders ................. H01S 5/141 356/497 | |
| 2010/0134803 A1 | 6/2010 | Baier et al. | |
| 2010/0142567 A1 | 6/2010 | Ward et al. | |
| 2011/0051143 A1 | 3/2011 | Flanders et al. | |
| 2011/0051148 A1 | 3/2011 | Flanders et al. | |
| 2011/0080591 A1 | 4/2011 | Johnson et al. | |

OTHER PUBLICATIONS

Eigenwillig, Christoph M., et al., "Wavelength swept ASE source," Optical Coherence Tomography and Coherence Techniques IV, edited by Peter E. Andersen, et al., Proc. of SPIE-OSA Biomedical Optics, SPIE-OSA, vol. 7372, 2009, pp. 737200-1 to 737200-6.

Huber, Robert et al., "Buffered Fourier domain mode locking: unidirectional swept laser sources for optical coherence tomography imaging at 370,000 lines/s," Optics Letters, vol. 31, No. 20, Oct. 15, 2006, pp. 2975-2977.

Huber, R., et al., "Fourier domain mode locking at 1050 nm for ultra-high-speed optical coherence tomography of the human retina at 236,000 axial scans per second," Optics Letters, vol. 32, No. 14, Jul. 15, 2007, pp. 2049-2051.

International Preliminary Report on Patentability and the Written Opinion of the International Searching Authority mailed Jul. 11, 2013, from counterpart International Application No. PCT/US2011/067164 filed on Dec. 23, 2011.

International Search Report and the Written Opinion of the International Searching Authority mailed Jun. 11, 2012 from counterpart International Patent Application No. PCT/US2011/067164, filed on Dec. 23, 2011.

International Search Report dated Jun. 11, 2012 from counterpart International Patent Application No. PCT/US2011/067164, filed on Dec. 23, 2011.

Kray, S., et al., "High-resolution simultaneous dual-band spectral domain optical coherence tomography," Optics Letters, vol. 34, No. 13, Jul. 1, 2009, pp. 1970-1972.

Leung, Michael K. K., et al., "Simultaneous 6-channel optical coherence tomography using a high-power telescope-less polygon-based swept laser in dual-amplifier configuration," Optical Coherence Tomography and Coherence Domain Optical Methods in Biomedicine XIV, edited by Joseph A. Izatt, et al., Proc. of SPIE, vol. 7554, 2010, pp. 755418-1 to 755418-6.

Oh, Wang-Yuhl, et al., ">400 kHz repetition rate wavelength-swept laser and application to high-speed optical frequency domain imaging," Optics Letters, vol. 35, No. 17, Sep. 1, 2010, pp. 2919-2921.

Sacchet, D., et al., "Simultaneous dual-band ultra-high resolution full-field optical coherence tomography," Optics Express, vol. 16, No. 24, Nov. 24 2008, pp. 19434-19446.

Spöler, F., "Simultaneous dual-band ultra-high resolution optical coherence tomography," Optics Express, vol. 15, No. 17, Aug. 20, 2007, pp. 10832-10841.

Wieser, Wolfgang, et al., "Multi-Megahertz OCT: High quality 3D imaging at 20 million A-scans and 4.5 GVoxels per second," Optics Express, vol. 18, No. 14, Jul. 5, 2010, pp. 14685-14704.

Zhou, C. et al., "Dual channel dual focus optical coherence tomography for imaging accommodation of the eye," Optics Express, vol. 17, No. 11, May 25, 2009, pp. 8947-8955.

\* cited by examiner

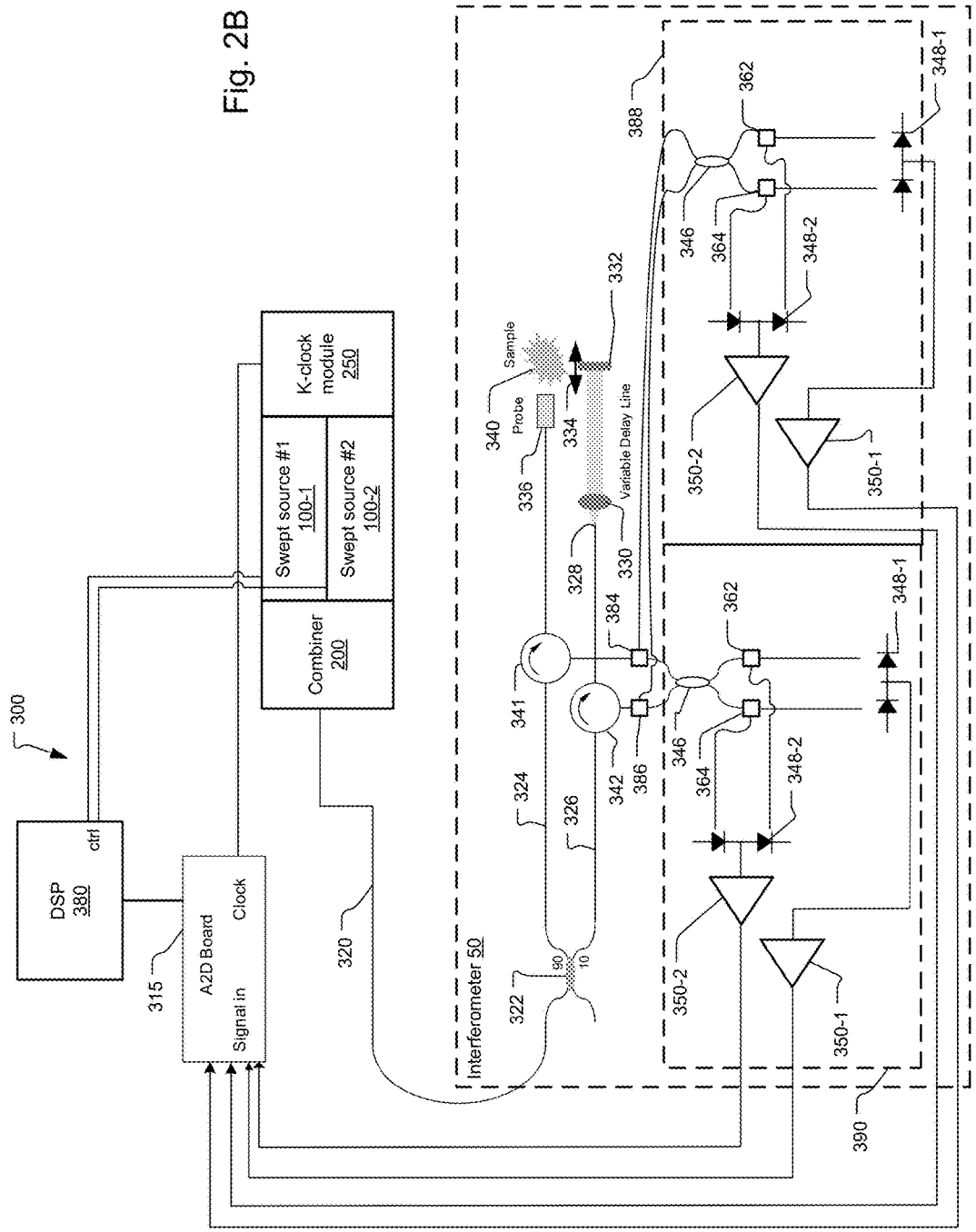

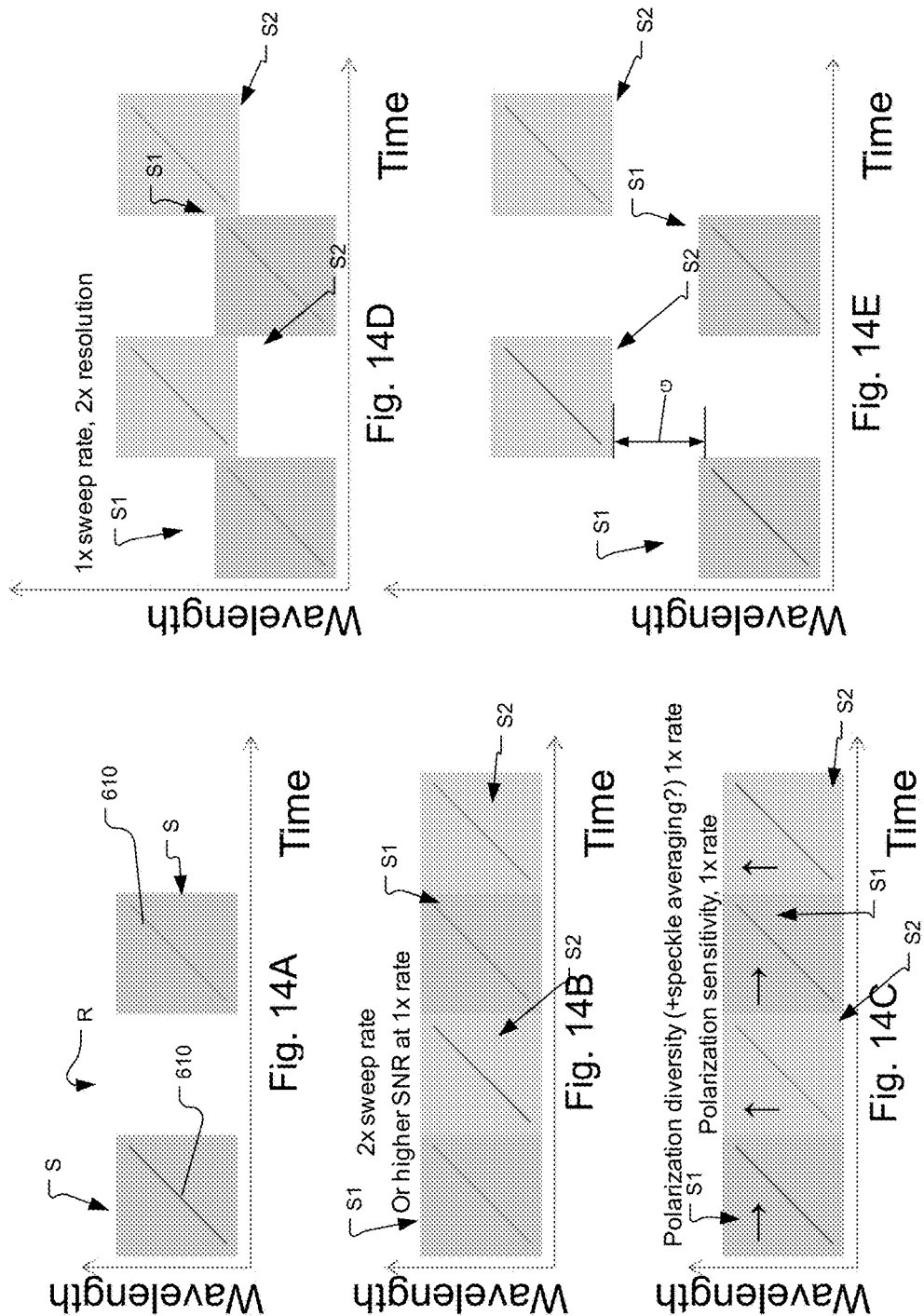

INTEGRATED DUAL SWEPT SOURCE FOR OCT MEDICAL IMAGING

RELATED APPLICATIONS

This application is a Divisional of U.S. application Ser. No. 12/980,144, filed on Dec. 28, 2010, which is incorporated herein by reference in its entirety.

BACKGROUND OF THE INVENTION

Optical coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform usually high-resolution cross sectional imaging. It is often applied to imaging biological tissue structures, for example, on microscopic scales in real time. Optical waves are reflected from an object or sample and a computer produces images of cross sections of the object by using information on how the waves are changed upon reflection.

The original OCT imaging technique was time-domain OCT (TD-OCT), which used a movable reference mirror in a Michelson interferometer arrangement. In order to increase performance, variants of this technique have been developed using two wavelengths in so-called dual band OCT systems.

In parallel Fourier domain OCT (FD-OCT) techniques have been developed. One example is time-encoded OCT, which uses a wavelength swept source and a single detector: it is sometimes referred to as time-encoded FD-OCT (TEFD-OCT) or swept source OCT. Another example is spectrum encoded OCT, which uses a broadband source and spectrally resolving detector system and is sometimes referred to as spectrum-encoded FD-OCT or SEFD-OCT.

These various OCT techniques offer different performance characteristics. FD-OCT has advantages over TD-OCT in speed and signal-to-noise ratio (SNR). Of the two FD-OCT techniques, swept-source OCT has distinct advantages over spectrum-encoded FD-OCT because of its capability of balanced and polarization diversity detection; it has advantages as well for imaging in wavelength regions where inexpensive and fast detector arrays, which are typically required for SEFD-OCT, are not available.

Swept source OCT has advantages in some additional respects. The spectral components are not encoded by spatial separation, but they are encoded in time. The spectrum is either filtered or generated in successive frequency steps and reconstructed before Fourier-transformation. Using the frequency scanning swept source, the optical configuration becomes less complex but the critical performance characteristics now reside in the source and especially its tuning speed and accuracy.

The swept sources for TEFD-OCT systems have been typically tunable lasers. The advantages of tunable lasers include high spectral brightness and relatively simple optical designs. The typical tunable laser is constructed from a gain medium, such as a semiconductor optical amplifier (SOA) and a tunable filter such as a rotating grating, grating with a rotating mirror, or a Fabry-Perot tunable filter. Currently, some of the highest speed TEFD-OCT lasers are based on the laser designs described in U.S. Pat. No. 7,415,049 B1, entitled Laser with Tilted Multi Spatial Mode Resonator Tuning Element, by D. Flanders, M. Kuznetsov and W. Atia. This highly integrated design allows for a short laser cavity that keeps the round-trip optical travel times within the laser short so that the laser is fundamentally capable of high speed tuning. Secondly, the use of micro-electro-mechanical system (MEMS) Fabry-Perot tunable filters combines the capability for wide spectral scan bands with the low mass, high mechanical resonant frequency deflectable MEMS membranes that have the capacity for high speed tuning.

Another class of swept sources that has the potential to avoid inherent drawbacks of tunable lasers is filtered amplified spontaneous emission (ASE) sources that combine a broadband light source, typically a source that generates light by ASE, with tunable filters and amplifiers.

Some of the highest speed devices based on filtered ASE sources are described in U.S. Pat. No. 7,061,618 B2, entitled Integrated Spectroscopy System, by W. Atia, D. Flanders P. Kotidis, and M. Kuznetsov, which describes spectroscopy engines for diffuse reflectance spectroscopy and other spectroscopic applications. A number of variants of the filtered ASE swept source are described, including amplified versions and versions with tracking filters.

More recently Eigenwillig, et al. have proposed a variant configuration of the filtered ASE source in an article entitled "Wavelength swept ASE source", Conference Title: Optical Coherence Tomography and Coherence Techniques IV, Munich, Germany, Proc. SPIE 7372, 73720O (Jul. 13, 2009). The article describes an SOA functioning both as an ASE source and first amplification stage. Two Fabry-Perot tunable filters are used in a primary-tracking filter arrangement, which are followed by a second SOA amplification stage. Also, U.S. patent application Ser. No. 12/553,295, filed on Sep. 3, 2009, entitled Filtered ASE Swept Source for OCT Medical Imaging, by D. Flanders, W. Atia, and M. Kuznetsov, which is incorporated herein in its entirety by this reference, lays out various integrated, high speed filtered ASE swept source configurations. U.S. patent application Ser. No. 12/776,373, entitled ASE Swept Source with Self-Tracking Filter for OCT Medical Imaging, filed on May 8, 2010, by the same inventors, outlines still further configurations that rely on the use of a self-tracking filter arrangement that can improve performance both in terms of speed and linewidth, among other things, and which is also incorporated herein in its entirety by this reference.

SUMMARY OF THE INVENTION

Aspects of the present invention are directed to swept source systems that include multiple swept sources. It further concerns optical coherence tomography systems that incorporate and are compatible with such swept source systems.

In general, according to one aspect, the invention features a laser system that comprises multiple laser sources. Specifically a first laser source generates a first tunable optical signal that is tuned over a first spectral scan band, the first laser source having first laser cavity defined by a first reflector and a shared reflector, the first laser source including a first gain element for amplifying light in the first laser cavity and a first tuning element for dictating a wavelength of the first optical signal. A second laser source generates a second tunable optical signal that is tuned over a second spectral scan band, the second laser source having a second laser cavity defined by a second reflector and the shared reflector, the second laser source including a second gain element for amplifying light in the second laser cavity and a second tuning element for dictating a wavelength of the second optical signal. An intracavity combiner located between the shared reflector and each of the first reflector and second reflector couples light to the shared reflector and back into the first laser cavity and the second laser cavity.

In embodiments, a combined optical signal including the first optical signal and the second optical signal is extracted through the shared reflector. Also, at least one birefringence compensation element is preferably provided in at least one of the first laser cavity and the second laser cavity for controlling a polarization of light returning to the first gain element and/or the second gain element.

Preferably, the intracavity combiner comprises polarization beam splitter for dividing light returning from the shared reflector between the first gain element and the second gain element. Here, a polarization rotation element in one of the first laser cavity and the second laser cavity is useful for rotating the polarization of light received by the polarization beam splitter. However, a polarization rotation element is provided in each of the first laser cavity and the second laser cavity for rotating the polarization of light received by the polarization beam splitter, in other examples. A combined optical signal including the first optical signal and the second optical signal can be extracted through the polarization beam splitter.

In other embodiments, the intracavity combiner comprises beam splitter for dividing light returning from the shared reflector between the first gain element and the second gain element. In other implementations, WDM combiners and beam switches are used.

In the typical application, the laser system is used in an OCT system that comprises an interferometer for dividing a combined optical signal, including the first tunable optical signal and the second tunable optical signal, between a reference arm leading to a reference reflector and a sample arm leading to a sample and a detector system for detecting an interference signal generated from the combined optical signal from the reference arm and from the sample arm.

Depending on the embodiment, the first spectral scan band and the second spectral scan band are substantially the same, non-overlapping spectral scan bands, or contiguous spectral scan bands.

In general, according to another aspect, the invention features an optical coherence analysis system that comprises a first swept source that generates a first optical signal that is tuned over a first spectral scan band, a second swept source that generates a second optical signal that is tuned over a second spectral scan band, a combiner for combining the first optical signal and the second optical signal for form a combined optical signal, an interferometer for dividing the combined optical signal between a reference arm leading to a reference reflector and a sample arm leading to a sample, a multi channel k-clock system for receiving the combined optical signal and separately detecting the first optical signal to generate a first clock and the second optical signal to generate a second clock, and a detector system for detecting an interference signal generated from the combined optical signal from the reference arm and from the sample arm in response to the first clock and the second clock.

In general, according to still another aspect, the invention features an optical coherence analysis system comprising: a first swept source that generates a first optical signal that is tuned over a first spectral scan band, a second swept source that generates a second optical signal that is tuned over a second spectral scan band, a combiner for combining the first optical signal and the second optical signal to form a combined optical signal, an interferometer for dividing the combined optical signal between a reference arm leading to a reference reflector and a sample arm leading to a sample, a coherence analysis detector system for detecting an interference signal generated from the first optical signal, and a spectral analysis detector for detecting the second optical signal after interaction with the sample.

In general, according to still another aspect, the invention features an optical coherence analysis system comprising a micro optical bench, a first ASE swept source that generates a first optical signal on the micro optical bench, a second ASE swept source that generates a second optical signal on the micro optical bench, a combiner, on the optical bench, for combining the first optical signal and the second optical signal for form a combined optical signal, an interferometer for dividing the combined optical signal between a reference arm leading to a reference reflector and a sample arm leading to a sample, a k-clock system, on the micro optical bench, for receiving the combined optical signal to generating a clock, and a detector system for detecting an interference signal generated from the combined optical signal from the reference arm and from the sample arm in response to the clock signal.

In general, according to still another aspect, the invention features an optical coherence analysis system comprising a first swept source that generates a first optical signal that is tuned over a first spectral scan band, a second swept source that generates a second optical signal that is tuned over a second spectral scan band, a combiner for combining the first optical signal and the second optical signal to form a combined optical signal, an interferometer for dividing the combined optical signal between a reference arm leading to a reference reflector and a sample arm leading to a sample, a coherence analysis detector system for detecting an interference signal generated from the first optical signal and the second optical signal, the coherence analysis detector system comprising WDM filters for separating the combined optical signals from the reference arm and the sample arm between a first detector subsystem that generates interference signals from the first optical signal and a second detector subsystem that generates interferences signals from the second optical signal.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2B is a schematic view of an OCT system with a dual swept source according to another embodiment of the invention incorporating a polarization sensitive optical receiver functioning at multiple wavelengths;

FIGS. 14A-14F are plots of wavelength as a function of time showing swept source scanning, with FIG. 14A showing conventional scanning. FIG. 14B showing time multiplexed scanning over a common scan band, FIG. 14C showing time multiplexed scanning over a common scan band with polarization diversity, FIG. 14D showing time multiplexed scanning over a different contiguous scan bands, FIG. 14E showing time multiplexed scanning over different, non-overlapping scan bands with a guard band, and FIG. 14F showing simultaneous scanning over a different scan bands;

DETAILED DESCRIPTION OF THE PREFERRED EMBODIMENTS

Figure 1:
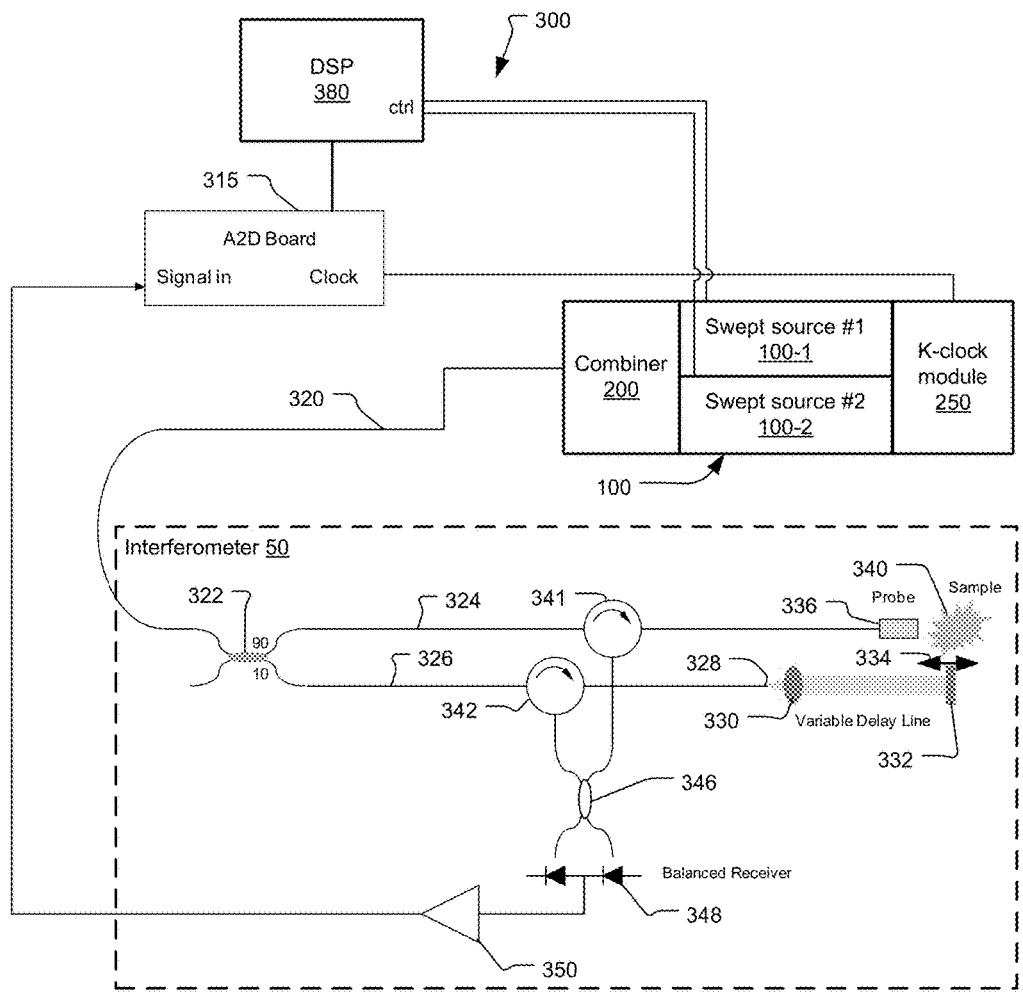
FIG. 1 is a schematic view of an OCT system with a dual swept source according to an embodiment of the invention.

FIG. 1 shows an optical coherence analysis system 300 using the integrated dual swept source 100, which has been constructed according to the principles of the present invention.

The integrated dual swept source system 100 generates a combined optical signal on optical fiber 320 that is transmitted to interferometer 50. In the preferred embodiment, this combined optical signal is a tunable optical signal that scans over a combined scanband with a narrowband emission.

The integrated dual swept source system 100 comprises at least a first swept source 100-1 and a second swept source 100-2. Each of these individual swept sources generates respective tunable optical signals, a first optical signal and a second optical signal. The first optical signal and the second optical signal are combined into the combined optical signal by a combiner 200 and coupled onto the optical fiber 320.

In one embodiment, the first swept source 100-1 and a second swept source 100-2 of the integrated dual swept source system 100 are operated in a time-multiplexed "ping-pong" fashion. At any given instant, the combined optical signal on optical fiber 320 is derived from only one of the swept sources 100-1, 100-2.

Preferably, the integrated dual swept source system 100 also further comprises a k-clock module 250. The k-clock module generates a clocking signal at equally spaced optical frequency increments as the combined tunable optical signal is timed over the combined scan band.

In the current embodiment, a Mach-Zehnder-type interferometer 50 is used to analyze the optical signals from the sample 340. The combined tunable signal from the swept source module 100 is transmitted on fiber 320 to a 90/10 optical coupler 322. The combined tunable signal is divided by the coupler 322 between a reference arm 326 and a sample arm 324 of the system.

The optical fiber of the reference arm 326 terminates at the fiber endface 328. The light exiting from the reference arm fiber endface 328 is collimated by a lens 330 and then reflected by a mirror 332 to return back, in some exemplary implementations.

The external mirror 332 has an adjustable fiber to mirror distance (see arrow 334), in one example. This distance determines the depth range being imaged, i.e. the position in the sample 340 of the zero path length difference between the reference arm 326 and the sample arm 324. The distance is adjusted for different sampling probes and/or imaged samples. Light returning from the reference mirror 332 is returned to a reference arm circulator 342 and directed to a 50/50 fiber coupler 346.

The fiber on the sample arm 324 terminates at the sample arm probe 336. The exiting light is focused by the probe 336 onto the sample 340. Light returning from the sample 340 is returned to a sample arm circulator 341 and directed to the 50/50 fiber coupler 346. The reference arm signal and the sample arm signal are combined in the fiber coupler 346 to generate an interference signal. The interference signal is detected by a balanced receiver, comprising two detectors 348, at each of the outputs of the fiber coupler 346. The electronic interference signal from the balanced receiver 348 is amplified by amplifier 350.

In one mode of operation, the first swept source 100-1 and a second swept source 100-2 are operated in a time-multiplexed "ping-pong" fashion. Only, a single channel receiver is required to detect the interference signal.

An analog to digital converter system 315 is used to sample the interference signal output from the amplifier 350. Frequency clock and sweep trigger signals derived from the k-clock module 250 of the dual swept source 100 are used by the analog to digital converter system 315 to synchronize system data acquisition with the frequency tuning of the swept source system 100.

Once a complete data set has been collected from the sample 340 by spatially raster scanning the focused probe beam point over the sample, in a Cartesian geometry, x-y, fashion or a cylindrical geometry theta-z fashion, and the spectral response at each one of these points is generated from the frequency tuning of the dual swept source 100, the digital signal processor 380 performs a Fourier transform on the data in order to reconstruct the image and perform a 2D or 3D tomographic reconstruction of the sample 340. This information generated by the digital signal processor 380 can then be displayed on a video monitor.

In one application, the probe 336 is inserted into blood vessels and used to scan the inner wall of arteries and veins. In other examples, other analysis modalities are included in the probe such as intravascular ultrasound (IVUS), forward looking IVUS (FLIVUS), high-intensity focused ultrasound (HIFU), pressure sensing wires and image guided therapeutic devices.

Figure 2A:
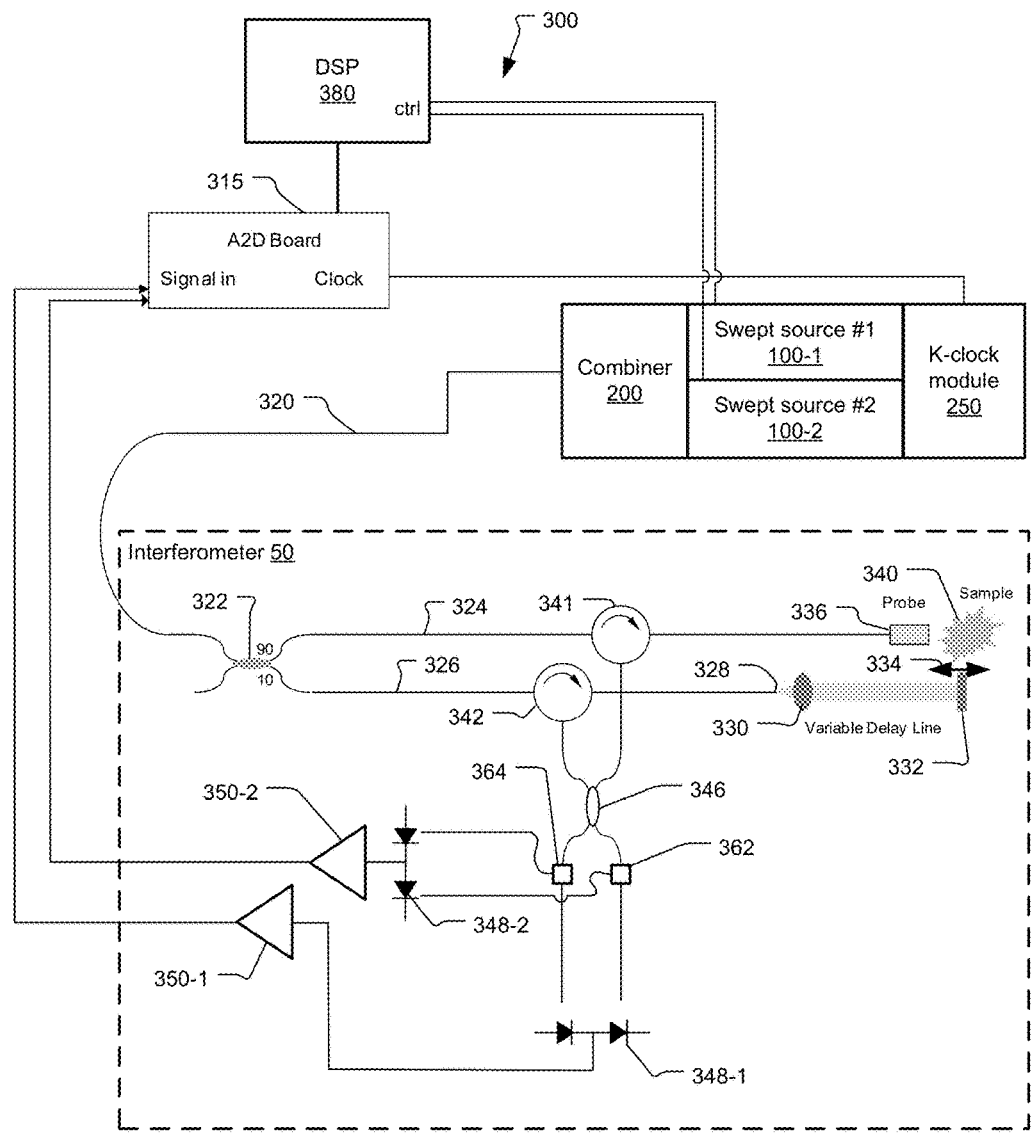
FIG. 2A is a schematic view of an OCT system with a dual swept source according to another embodiment of the invention incorporating a wavelength and/or polarization diversity optical receiver.

FIG. 2A shows an optical coherence analysis system 300 that provides for polarization sensitive coherence analysis.

In this second embodiment, the dual swept source 100 and specifically the first swept source 100-1 and the second swept source 100-2 are preferably operated in a time multiplexed fashion.

The detector system has the capacity to separate the interference signal into two orthogonal polarizations. Polarization beam splitters 362 and 364 separate the polarizations which are then detected by two balanced detectors 348-1 and 348-2. Separate amplifiers 350-1 and 350-2 are provided, and the analog to digital conversion board 315 includes two channels to enable simultaneous detection of the output of amplifiers 350-1 and 350-2.

FIG. 2B shows an optical coherence analysis system 300 that provides for polarization sensitive detection at two wavelengths simultaneously.

Here, the dual swept source 100 and specifically the first swept source 100-1 and the second swept source 100-2 are not necessarily operated in a time multiplexed fashion. At least, it is not a requirement of the architecture that they are operated in this fashion. Instead, the first tunable optical signal from the first swept source 100-1 and the second tunable optical signal from the second swept source 100-2 are separated in wavelength. As a result, the combined optical signal on optical fiber 320 in one implementation of this embodiment is at any instant a combination of the first tunable optical signal and the second tunable optical signal, which are tunable over different spectral bands.

The detector system has the capacity to separate the reference and sample arms signals into portions derived from first tunable optical signal and the second tunable optical signal prior to detection. A first wavelength division multiplexing (WDM) splitter 384 and a second WDM splitter 386 are used to separate the spectral components of the signals from the circulators 341, 342. The separate spectral components are sent to two separate detector subsystems 388, 390. In this implementation, it is not a requirement of the architecture that the first swept source 100-1 and the second swept source 100-2 are operated in this fashion. Instead, the first tunable optical signal from the first swept source 100-1 and the second tunable optical signal from the second swept source 100-2 are separated in wavelength. The two separate detector subsystems 388, 390 are used to separately detect the interference signals that result from the first tunable optical signal from the first swept source 100-1 and the second tunable optical signal that is generated by the second swept source 100-2.

In more detail, each of the first detector subsystem 388 and the second detector subsystem 390 has a fiber coupler 346 for generating interference signals. Polarization beam splitters 362 and 364 then separate the interference signals into the separate orthogonal polarizations to enable polarization sensitive detection. Two balanced detectors 348-1 and 348-2 in each the detector subsystems 388, 390 separately detect the interference signals that result from the first tunable optical signal from the first swept source 100-1 and the second tunable optical signal that is generated by the second swept source 100-2. Separate amplifiers 350-1 and 350-2 are provided, and the analog to digital conversion board 315 includes four channels to enable simultaneous detection of the output of amplifiers 350-1 and 350-2 from each the detector subsystems 388, 390.

It should be noted that while the illustrated embodiment is shown with two swept-sources and two detection channels, more than two swept sources and more than two corresponding detection channels are used in still further embodiments. In such implementations, a WDM combiner 200 is used to combine multiple swept sources 100-1 to 100-n, such as n=4 or 6 or more sources. WDM splitters 384, 386 are then used to separate out the signals associated with the different swept sources for detection at multiple detector subsystems 388, 390.

Figure 3:
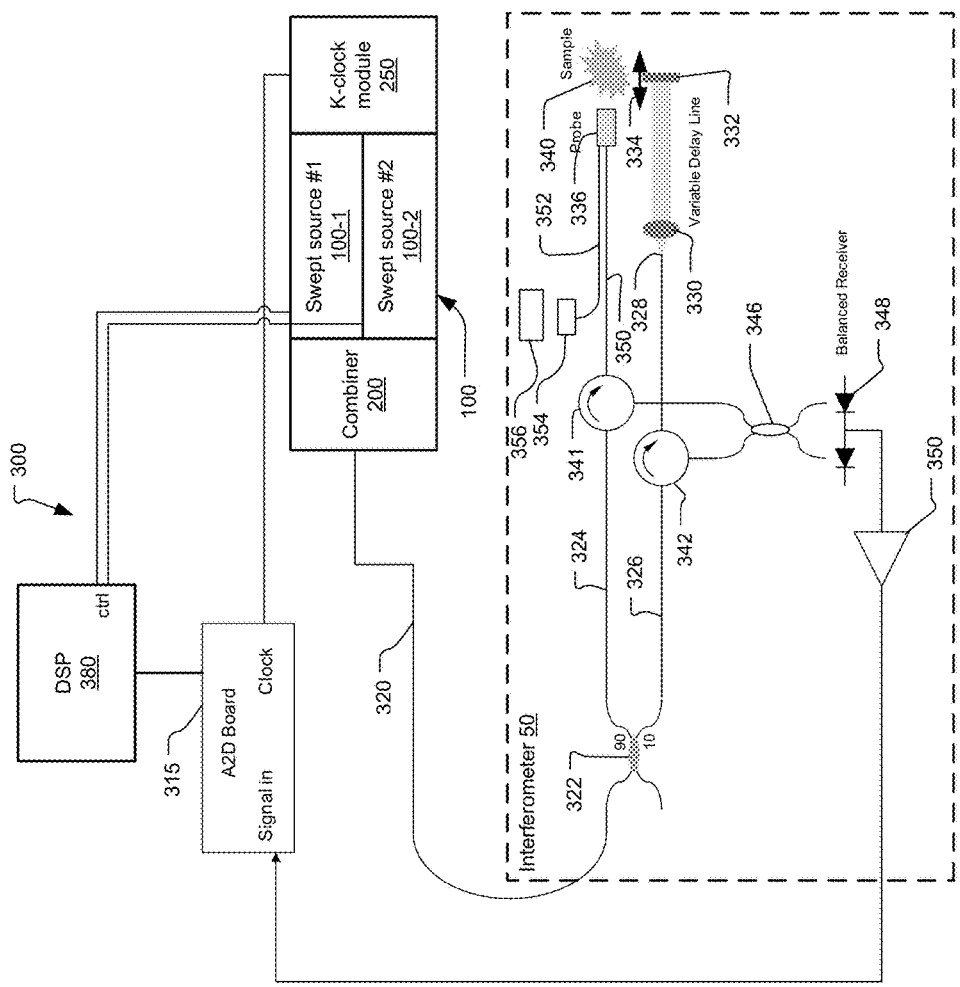
FIG. 3 is a schematic view of an OCT system with a dual swept source according to another embodiment of the invention incorporating spectral analysis functionality.

FIG. 3 shows an optical coherence analysis system 300 that has been constructed according to a third embodiment of the present invention.

This third embodiment includes the capability to perform spectroscopic analysis on the sample 340.

In more detail, in the preferred embodiment, two optical fibers are provided to the probe 336. Optical fiber 350 transmits the combined signal including first tunable optical signal and the second tunable optical signal to the probe 336, which directs the signals to the sample 340. Light returning from the sample 340 that is used for optical coherence analysis returns on optical fiber 350 to circulator 341. This returning light is processed as described in the previous embodiments to generate an optical coherence analysis of the sample 340.

In contrast, light that is used for spectral analysis of the sample 340 is coupled from the probe on optical fiber 352. This spectral analysis light is detected by spectral analysis detector 356. In one implementation, a filter and collimator element 354 is used to direct the light onto the spectral analysis detector 356 and also possibly remove any spectral components of the signal that are related to the optical coherence analysis of the sample 340.

In one implementation, the first swept source 100-1 is used for optical coherence analysis. The second swept source 100-2 is used for spectral analysis of the sample 340. Typically, these two swept sources will operate with different spectral scan bands. In this implementation, the filter and collimator element 354 is a WDM filter that transmits only the scanband generated by the second swept source 100-2.

In still a further implementation, the spectral analysis of the sample 340 is performed at the same spectral regions as the optical coherence analysis. In this case the filter and collimator element 354 passes the spectral components associated with both the first swept source 100-1 and the second swept source 100-2 and the detector 356 detects the spectral response of the sample 340 in a time multiplexed fashion. Alternatively, when the first swept source 100-1 in the second swept source 100-2 operate in different spectral scan bands, then the filter and collimator element 354 allows the light from only one of these scan bands to reach the detector 356 when they cannot be separated in time.

Figure 4:
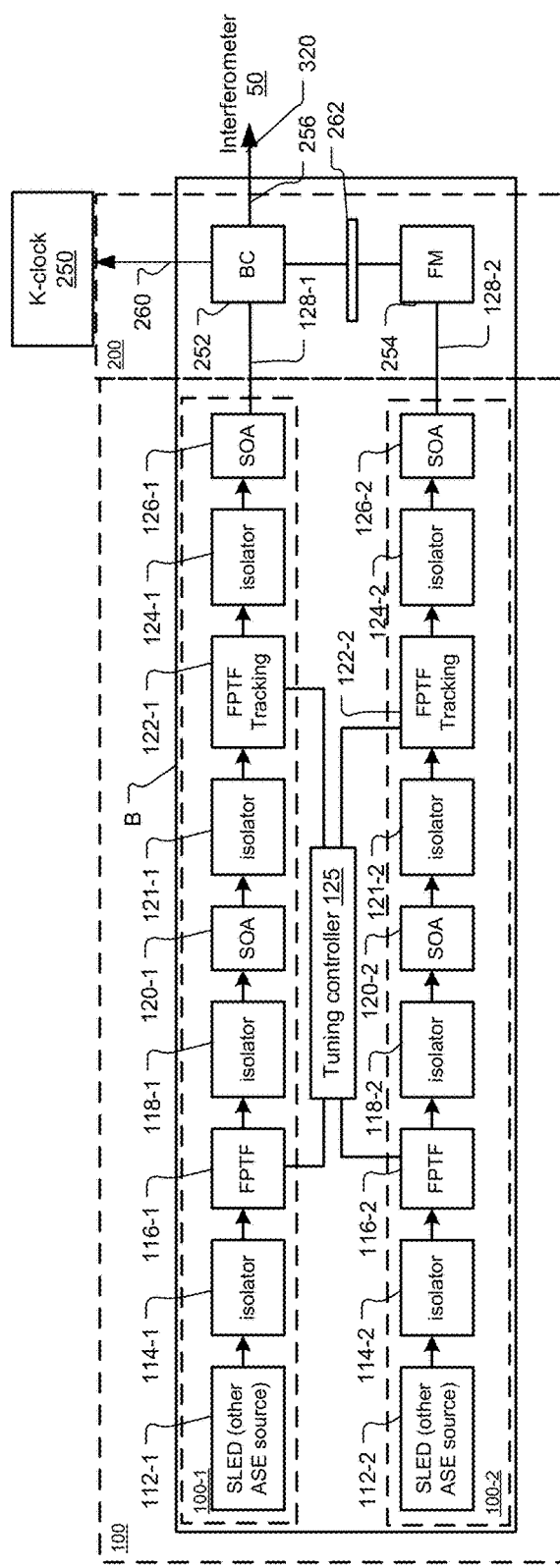
FIG. 4 is a block diagram of a dual filtered ASE swept optical source.

FIG. 4 shows a first embodiment of the dual swept optical source 100 that has been constructed according to the principles of the present invention.

The first and the second swept sources 100-1 and 100-2 are each filtered amplified spontaneous emission sources. In the current embodiments these ASE swept sources 100-1 and 100-2 are any one of ASE swept sources described in U.S. patent application Ser. No. 12/553,295, entitled Filtered ASE Swept Source for OCT Medical Imaging, filed on Sep. 3, 2009 by Flanders, et al. or in U.S. patent application Ser. No. 12/776,373, entitled ASE Swept Source with Self-Tracking Filter for OCT Medical Imaging, filed on May 8, 2010. Additionally, other amplified ASE swept sources could be used in still further examples. Nevertheless, the following example is provided based on one of the swept source configurations of this incorporated document.

In more detail, the swept sources 100-1, 100-2 each comprise a broadband source 112-1, 112-2 that generates a broadband optical signal. In general, the broadband signal is characterized by a continuous spectrum that extends in wavelength over at least 40 nanometers (nm) of bandwidth, full width half maximum (FWHM). Typically, the continuous spectrum extends over at least 70 nm and preferably over 100 nm or greater.

In the preferred embodiment, the broadband sources 112-1, 112-2 are electrically pumped semiconductor chip gain media that are bonded or attached to a common bench B. Examples of the sources 112-1, 112-2 include superluminescent light emitting diodes (SLED) and semiconductor optical amplifiers (SOA). The material systems of the chips are selected based on the desired spectral operating range for each of the first and the second swept sources 100-1 and 100-2. Common material systems are based on III-V semiconductor materials, including binary materials, such as GaN, GaAs, InP, GaSb, InAs, as well as ternary, quaternary, and pentenary alloys, such as InGaN, InAlGaN, InGaP, AlGaAs, InGaAs, GaInNAs, GaInNAsSb, AlInGaAs, InGaAsP, AlGaAsSb, AlGaInAsSb, AlAsSb, InGaSb, InAsSb, and InGaAsSb. Collectively, these material systems support operating wavelengths from about 400 nm to 2000 nm, including longer wavelength ranges extending into multiple micrometer wavelengths. Semiconductor quantum well and quantum dot gain regions are typically used to obtain especially wide gain and spectral emission bandwidths. Currently, edge-emitting chips are used although vertical cavity surface emitting laser (VCSEL) chips are used in different implementations.

The use of semiconductor chip gain media for the first and the second swept sources 100-1 and 100-2 has advantages in terms of system integration since these semiconductor chips can be bonded to submounts that in turn are directly bonded to the common bench B. Other possible gain media can be used in other implementations, however. In these examples, the broadband signal is typically transmitted via optical fiber to the bench B. Such examples include solid state gain media, such as rare-earth (e.g., Yb, Er, Tm) doped bulk glass, waveguides or optical fiber.

In these examples, the output facets of the chips or gain waveguides/fibers are antireflection coated, and possibly angled, so that the gain media do not lase but instead generate broadband light via amplified spontaneous emission (ASE).

In some embodiments, the broadband sources 112-1, 112-2 have different operating or spectral emissions to form separate non-overlapping spectral bands. In other examples, the spectral bands of the broadband sources 112-1, 112-2, are contiguous or potentially overlapping. As a result, the broadband sources 112-1, 112-2 are in some examples chips made out of different material systems.

The use of sources with complementary spectral bands enables the dual swept source system 100 to generate a combined tunable optical signal that covers a wider wavelength scanning range. This translates into a higher spatial (depth) resolution for the imaging system. Alternatively, the two different spectral bands can provide complementary information about the sample, such as different penetration depth into the sample and different sample image contrast. In still other embodiments, spectral bands are selected for the best optical coherence analysis and different spectral bands are selected for the spectral analysis of the sample.

The use of two swept sources with substantially the same spectral band but multiplexed in alternating time slots in a "ping pong" fashion allows higher duty cycle for data acquisition and better frequency tuning linearity of each of the two sources. This "ping pong" dual laser approach can be used advantageously instead of the standard optical buffering approach in high speed OCT, where two copies of the optical signal from a single swept source are time multiplexed after time delaying one of the signal copies in a long length of optical fiber. The advantage of the dual source approach is that, unlike the case with optical buffering, it does not require a long length of fiber with its possible strong dispersion that strongly degrades imaging resolution.

Another major benefit of the ping-pong approach is the 2× higher attainable duty cycle, which relaxes the maximum data acquisition frequency requirements for a given scan range and scan speed by a factor of 2, allowing for lower cost data acquisition components or faster scan speeds.

In other examples, the broadband sources 112-1, 112-2 generate broadband signals that have different polarizations, such as orthogonal polarizations. The advantage here is that the optical signals from the separate broadband sources provide polarization diversity sample illumination and signal detection such as to eliminate polarization sensitivity of the imaging system and eliminate polarization artifacts in the image. Alternatively, the two orthogonal polarizations can be used for polarization sensitive imaging that can enhance imaging contrast of specific regions of interest in the sample.

The bench B is termed a micro-optical bench and is preferably less than 20 millimeters (mm) in width and about 50 mm in length or less. This size enables the bench to be installed in a standard, or near standard-sized, butterfly or DIP (dual inline pin) hermetic package. In one implementation, the bench B is fabricated from aluminum nitride. A thermoelectric cooler is disposed between the bench B and the package (attached/solder bonded both to the backside of the bench and inner bottom panel of the package) to control the temperature of the bench B.

The broadband optical signals from the broadband sources 112-1, 112-2 are coupled to respective isolators 114-1, 114-2, which are preferably also bonded or attached to the bench B. These isolators 114-1, 114-2 prevent feedback into the broadband sources 112-1, 112-2 that might cause them to lase or otherwise change, e.g. produce ripple in, the emission spectrum of the broadband optical signal from the broadband sources.

First-stage tunable filters 116-1, 116-2 function as tunable bandpass filters to convert the broadband signals to narrow band tunable signals, the first and second tunable signals. In a current embodiment, the passband of the first stage tunable filters have a full width half maximum (FWHM) bandwidths of less than 20 or 10 GigaHertz (GHz), and are preferably 5 GHz or less. For spectroscopy this relatively narrow passband yields high spectral resolution. For optical coherence tomography, this high spectral resolution implies long coherence length of the source and therefore enables imaging deeper into samples, for example deeper than 5 mm. In lower performance applications, for example OCT imaging less than 1 mm deep into samples, broader FWHM passbands are sometimes appropriate, such as passbands of about 200 GHz or less.

The first-stage tunable filters 116-1, 116-2 are scanned over a first spectral scan band and a second spectral scan band, respectively. In some implementations, first spectral scan band and the second spectral scan bands are non-overlapping, contiguous, overlapping, or the same scan bands. Generally, the scan bands of first-stage tunable filters 116-1, 116-2 are matched to the corresponding emission spectral bands of the respective broadband sources 112-1, 112-2.

In the current embodiment, the first stage tunable filters 116-1, 116-2 are Fabry-Perot tunable filters that are fabricated using micro-electro-mechanical systems (MEMS) technology and are attached, such as directly solder bonded, to the bench B. Currently, the filters 116-1, 116-2 are manufactured as described in U.S. Pat. No. 6,608,711 or 6,373,632, which are incorporated herein by this reference. A curved-flat resonator structure is used in which a generally flat mirror and an opposed curved mirror define a filter optical cavity, the optical length of which is modulated by electrostatic deflection of at least one of the mirrors.

The tunable optical signals that are produced by the passband of the first stage tunable filters 116-1, 116-2 are amplified in first stage optical amplifiers 120-1, 120-2 of a first amplification stage. Preferably the first stage optical amplifiers are SOA's with antireflection coated and angled front and rear facets, enabling integration onto the bench B by attachment, typically via a submount.

Second isolators 118-1, 118-2 between the first stage tunable filters 116-1, 116-2 and the first amplifiers 120-1, 120-2 prevent back reflections between the front facets of the first amplifiers 120-1, 120-2 and the first stage tunable filters 116-1, 116-2 from causing lasing or other spectral ripple due to parasitic reflections between these two elements. The second isolators 118-1, 118-2 are preferably also bonded or otherwise attached to the bench B.

The amplified tunable signals from the first stage amplifiers 120-1, 120-2 are again passband filtered by second stage tunable filters 122-1, 122-2. These second stage filters 122-1, 122-2 are preferably tunable MEMS Fabry-Perot filters as described previously and are preferably also similarly solder-bonded or otherwise attached to the bench B. In some implementations, the only difference between the first stage tunable filters 116-1, 116-2 and the second stage tunable filters 122-1, 122-2 are that the second stage tunable filters 122-1, 122-2 have slightly broader passbands than the first stage tunable filters 116-1, 116-2, such as between 2 and 20 times broader in frequency. These second stage filters 122-1, 122-2 are termed tracking filters because they are controlled to scan synchronously with the first stage tunable filters 116-1, 116-2 and thus track tuning of the first stage filters. The tracking filters function primarily to remove ASE noise introduced by the first stage amplifiers 120-1, 120-2 and further spectrally shape and narrow the tunable signal.

The synchronous tracking of the second stage tunable filters 122-1, 122-2 with the first stage tunable filters 116-1, 116-2 is controlled by a tuning controller 125 that drives both filters of both stages and swept sources. Preferably, the tuning controller 125 spectrally centers the passbands of the tracking tunable filters 122-1, 122-2 on passbands of the first stage tunable filters 116-1, 116-2 and then tunes the two passbands together over the scanband extending over the gain bands of the respective broadband sources 112-1, 112-2 and amplifiers 120-1, 120-2, 126-1, 126-2.

Third isolators 121-1, 121-2 between the first stage amplifiers 120-1, 120-2 and the second stage tunable filters 122-1, 122-2 prevent back reflections between the back facets of the first stage amplifiers 120-1, 120-2 and the second stage tunable filters 122-1, 122-2 from causing lasing or other spectral ripple due to parasitic reflections between these two elements and any other intervening elements such as lenses, not shown in this view. The third isolators 121-1, 121-2 are preferably also bonded or otherwise attached to the bench B.

The amplified tunable optical signals that are produced from the first stage optical amplifiers 120-1, 120-2 and filtered by the tracking filters 122-1, 122-2 are again amplified in second amplifiers 126-1, 126-2 of a second amplification stage. Preferably the second stage optical amplifiers 126-1, 126-2 are also SOA's with antireflection coated and angled front and rear facets, enabling integration onto the bench B by attachment to it. In terms of control, the second stage optical amplifiers 126-1, 126-2 are usually operated in saturation with a lower input saturation power to minimize broadband ASE contribution from this last gain stage.

Fourth isolators 124-1, 124-2 between the front facets of the second stage amplifiers 126-1, 126-2 and the second stage tunable filters 122-1, 122-2 prevent back reflections between the front facet of the second amplifiers 126-1, 126-2 and the second tunable filters 122-1, 122-2 from causing lasing or other spectral ripple due to parasitic reflections between these elements. The fourth isolators 124-1, 124-2 are preferably also bonded or otherwise attached to the bench B.

If required, still further gain stages can be used. In one example third SOAs, third amplification stage, are added. For other applications having still higher power requirements, a rare-earth doped fiber gain stage is added after the second SOAs 126-1, 126-2.

The outputs of each second stage amplifiers 126-1, 126-2 are a first tunable optical signal 128-1 and a second tunable optical signal 128-2. These optical signals are combined in a combiner stage 200 to form a combined optical signal 256 on optical fiber 320. In the preferred embodiment, the elements of the combiner stage 200 are implemented on and secured to the optical bench B.

In one example, the combiner 200 forms the combined optical signal 256 using a WDM filter. In this implementation, a first spectral scan band and the second spectral scan band are non-overlapping spectral scan bands. A fold mirror 254 directs the second tunable optical signal 128-2 to a beam combining element 252, which is a WDM filter that reflects light in the second spectral scan band and transmits light in the first spectral scan band.

In another example, the first tunable optical signal 128-1 and the second tunable optical signal 128-2 have orthogonal polarizations. The signals are combined in the combined signal using a polarization beam combiner as the beam combining element 252. Since this example relies on polarization diversity, it works when the first spectral scan band and the second spectral scan band are the same, overlapping, contiguous, and non-overlapping. In order to produce the orthogonal polarizations a quarterwave plate 262 is typically added to the optical path of one of the sources.

In still another example, the first tunable optical signal 128-1 and the second tunable optical signal 128-2 are time multiplexed. Here, the signals are combined in the combined signal using a beam switch as the beam combining element 252 by alternately passing either the first tunable optical signal 128-1 or the second tunable optical signal 128-2 as the combined signal 256.

In still another example, the beam combining element 252 is a 50/50 beamsplitter/combiner, where the second optical output of such combiner is used in the input 260 to the K-clock module 250, which generates the k-clock signal for triggering analog-to-digital data acquisition electronics module 315.

Figure 5:
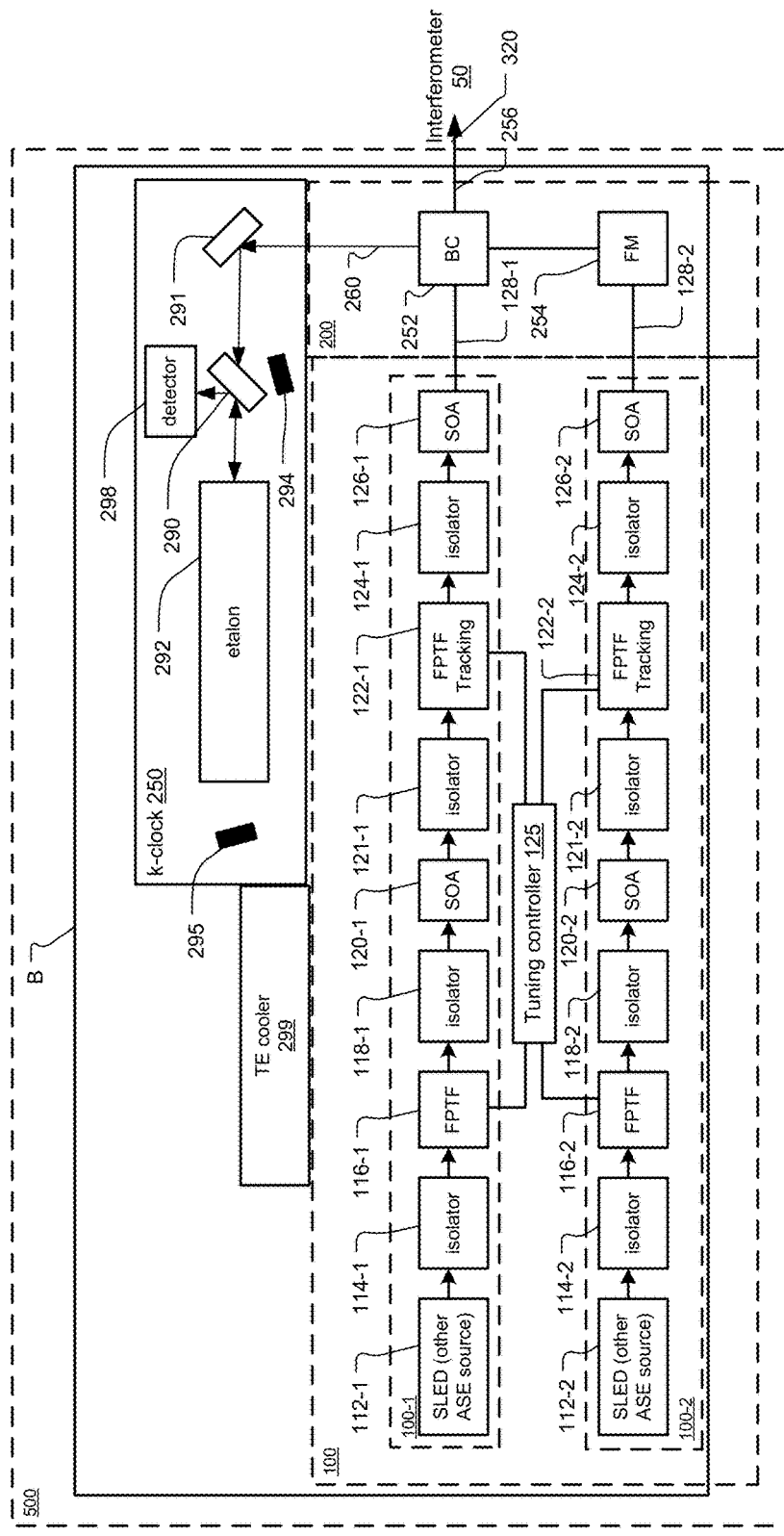
FIG. 5 is a block diagram of a dual filtered ASE swept optical source with an integrated k-clock system.

FIG. 5 shows another embodiment of the dual swept optical source 100 that has an integrated k-clock.

Particularly, the k-clock system 250 is integrated on the bench B along with the dual swept optical source 100. Preferably, the k-clock system 250 and the components of the dual swept optical source 100 are further integrated together within a common hermetic package 500.

The description presented above with respect to FIG. 4 generally applies FIG. 5. However, this embodiment differs in that it includes the integrated k-clock system 250.

In more detail, input beam 260 is the combined beam from the beam combiner 252. It is reflected by a fold mirror 291. The light then passes through a beam splitter 290, which is preferably a 50/50 splitter to a clock etalon 292. Any light reflected by the splitter 290 is directed to a beam dump component 294 that absorbs the light and prevents parasitic reflections in the hermetic package 500.

The clock etalon 292 functions as a spectral filter. Its spectral features are periodic in frequency and spaced spectrally by a frequency increment related to the length and refractive index of the constituent material of the clock etalon 292, which is fused silica in one example. The physical length of etalon 292 is L. The etalon can alternatively be made of other high-index and transmissive materials such as silicon for compactness, but the optical dispersion of the material may need to be compensated for with additional processing. Also, air-gap etalons, which are nearly dispersionless, are another alternative. Still a further alternative is a free-space interferometer (e.g. a Michelson), which also is dispersionless and is adjusted by moving the relative positions of the mirrors.

The contrast of the spectral features of the etalon 292 is determined by the reflectivity of its opposed endfaces. In one example, reflectivity at the etalon endfaces is provided by the index of refraction discontinuity between the constituent material of the etalon and the surrounding air, gas or vacuum. In other examples, the opposed endfaces are coated with metal or preferably dielectric stack mirrors to provide higher reflectivity and thus contrast to the periodic spectral features.

In the illustrated example, the clock etalon 292 is operated in reflection. The light returning from the clock etalon 292 and reflected by beamsplitter 290 is detected by detector 298. The light detected by detector 298 is characterized by drops and rises in power as the frequency of the combined tunable optical signal scans through the reflective troughs/reflective peaks provided by the clock etalon 298. Light transmitted by the etalon 292 is collected by beam dump 295.

The implementation of the k-clock system 250 on the bench B provides advantages in that a thermo electric cooler 299, that is also installed within the package 500, is used both to control the temperature of the swept source system 100 and temperature stabilize the k-clock system 250. Additional advantages are the small overall size of the system along with robustness against shock since all of the components are installed on a common rigid bench B.

Figure 6:
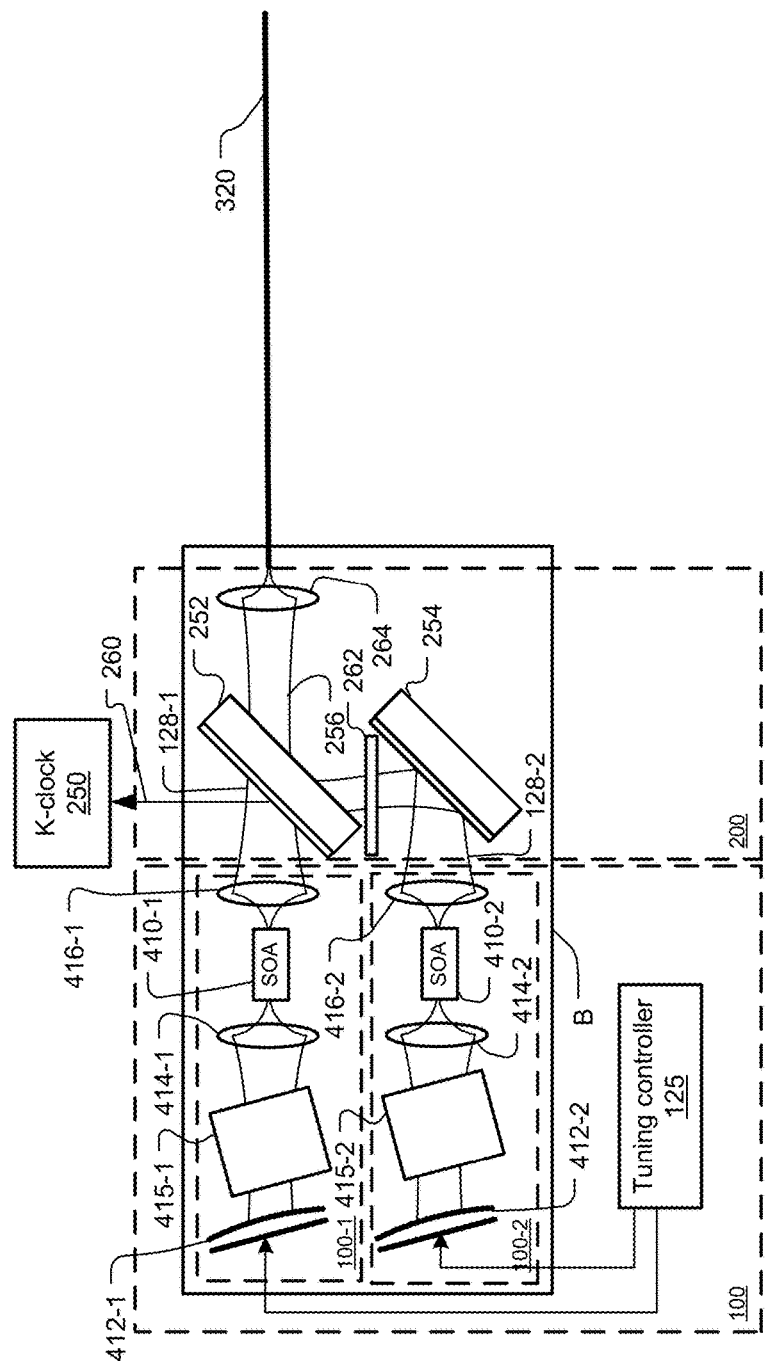
FIG. 6 is a schematic diagram of a dual laser swept optical source.

FIG. 6 shows another embodiment of the dual swept optical source 100, using laser sources, according to the principles of the present invention.

The first and the second laser swept sources 100-1 and 100-2 are each preferably lasers as described in incorporated U.S. Pat. No. 7,415,049 B1.

In more detail, each of the tunable lasers sources 100-1, 100-2 comprises a semiconductor gain chip 410-1, 410-2 that is paired with a micro-electro-mechanical (MEMS) angled reflective Fabry-Perot tunable filter 412-1, 412-2 to create external cavity tunable laser (ECL) on a common micro-optical bench B.

The semiconductor optical amplifier (SOA) chips 410-1, 410-2 are located within a laser cavity. In the current embodiment, input facets of the SOA chips 410-1, 410-2 are angled and anti-reflection (AR) coated, providing parallel beams from the two facets. The output facets are coated to define one end of the laser cavities, in one example.

Each facet of the SOAs 410-1, 410-2 has associated lenses 414-1, 414-2, 416-1, 416-2 that are used to couple the light exiting from either facet of the SOAs 410-1, 410-2. The first lenses 414-1, 414-2 couple the light between the front facets of the SOAs 410-1, 410-2 and the respective reflective Fabry-Perot tunable filter 412-1, 412-2. Light exiting out the output or front facets of the SOAs 410-1, 410-2 is coupled by second lenses 416-1, 416-2 to a combiner stage 200.

The angled reflective Fabry-Perot filters 412-1, 412-2 are a multi-spatial-mode tunable filters that provide angular dependent reflective spectral response back into the respective laser cavities. This phenomenon is discussed in more detail in incorporated U.S. Pat. No. 7,415,049 B1.

In one implementation, extender elements 415-1, 415-2 are added to the laser cavities. These are transparent high refractive index material, such as fused silica or silicon or other transmissive material having a refractive index of about 1.5 or higher. Currently silicon is preferred. Both endfaces of the extender elements 415-1, 415-2 are antireflection coated. Further, the elements are preferably angled by between 1 and 10 degrees relative to the optical axis of the cavities to further spoil any reflections from the endfaces from entering into the laser beam optical axis. These extender elements 415-1, 415-2 are used to change the optical distance between the laser intracavity spurious reflectors and thus change the depth position of the spurious peak in the image while not necessarily necessitating a change in the physical distance between the elements.

The combiner stage 200 forms a combined optical signal 256 from the first tunable optical signal 128-1 and the second tunable optical signal 128-2 generated by the tunable lasers 100-1, 100-2. In the preferred embodiment, the elements of the combiner stage 200 are implemented on and secured to the optical bench B. The combined optical signal is coupled by lens 264 into optical fiber 320 for transmission to the interferometer of the OCT system.

In one example, the combiner 200 forms the combined optical signal 256 using a WDM filter. In this implementation, a first spectral scan band of first tunable laser 100-1 and the second spectral scan band of second tunable laser 100-2 are non-overlapping spectral scan bands. A fold mirror 254 directs the second tunable optical signal 128-2 to a beam combining element 252, which is a WDM filter that reflects light in the second spectral scan band and transmits light in the first spectral scan band.

In another example, the first tunable optical signal 128-1 and the second tunable optical signal 128-2 have orthogonal polarizations. A quarter wave plate 262 is used to rotate the polarization of the second tunable optical signal 128-2 from the second tunable laser 100-2. In other examples, the SOA chips produce optical signals of orthogonal polarizations. The signals are combined in the combined optical signal 256 using a polarization beam combiner as the beam combining element 252. Since this example relies on polarization diversity, it works when the first spectral scan band and the second spectral scan band the same, overlapping, contiguous, and non-overlapping.

In still another example, the first tunable optical signal 128-1 and the second tunable optical signal 128-2 are time multiplexed. Here, the signals are combined in the combined signal 256 using a beam switch as the beam combining element 252 by alternately passing either the first tunable optical signal 128-1 or the second tunable optical signal 128-2 as the combined signal 256.

In still another example, the beam combining element 252 is a 50/50 beamsplitter/combiner, where the second optical output 260 of such combiner 252 is used in the K-clock module 250 for generating the k-clock signal for triggering analog-to-digital data acquisition electronics module 315.

Figure 7:
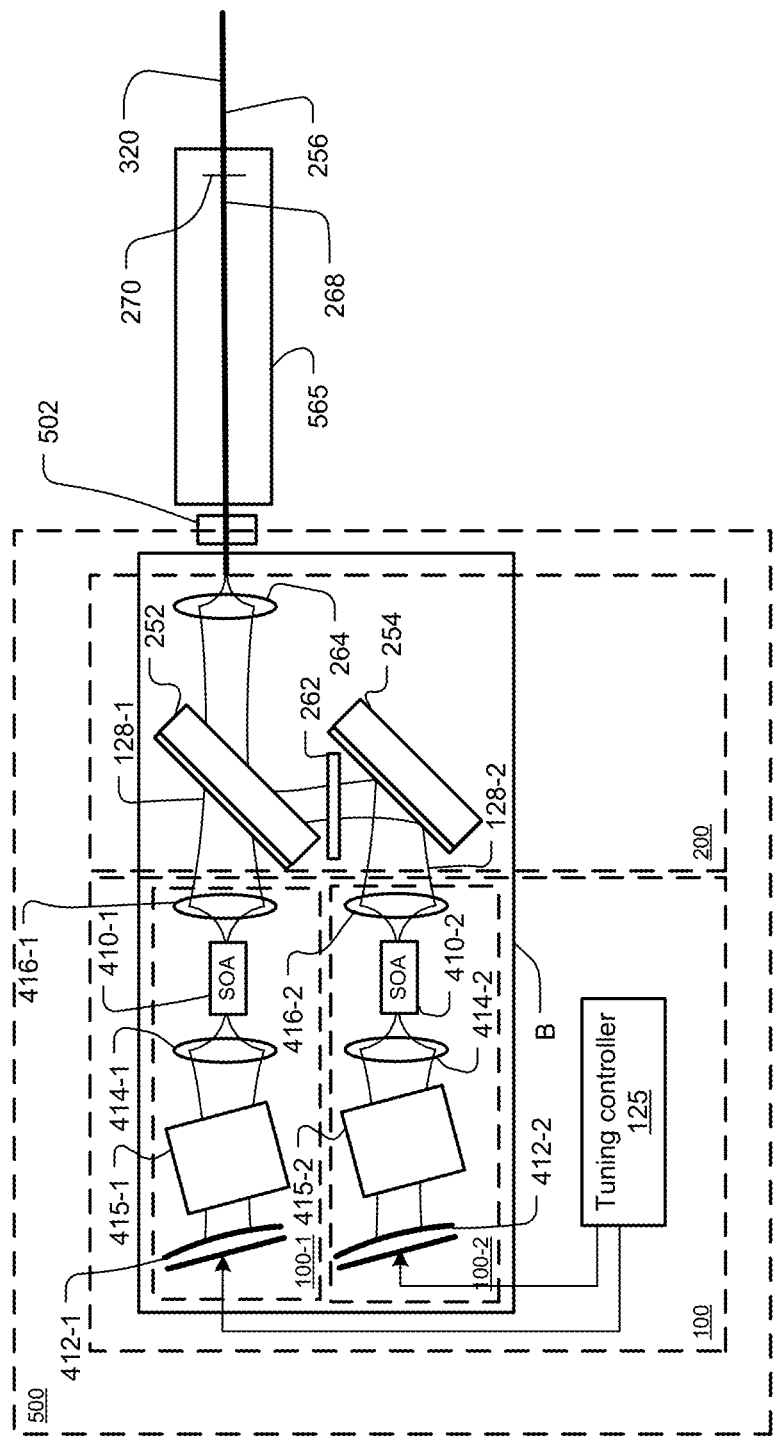
FIG. 7 is a schematic diagram of a dual laser swept optical source with a shared optical cavity according to the present invention.

FIG. 7 shows another embodiment of the dual swept optical source 100, using laser sources, according to the principles of the present invention.

In the embodiment of FIG. 6, the laser cavities are relatively short, extending between the tunable filters 412-1, 412-2 and the output facets of the SOAs 410-1, 410-2. The embodiment of FIG. 7 provides for longer tunable filter cavities by implementing a shared cavity arrangement in which tunable laser swept sources 100-1, 100-2 have a portion of the laser cavity that is shared between them.

In more detail, in this embodiment, both facets of the SOAs 410-1, 410-2 are antireflection coated. The optical cavities of each of the tunable laser swept sources 100-1, 100-2 extend from their respective tunable filters 412-1, 412-2 through the combiner stage 200 to a shared reflector 270. This shared reflector 270 is a common reflector that defines an end of the laser cavity for both of the tunable laser swept sources 100-1, 100-2.

In one implementation, the shared reflector 270 is a partially reflecting mirror formed on the end of a fiber pigtail 268 that is optically coupled to the bench B. Light from both laser cavities of tunable laser swept sources 100-1, 100-2 is coupled into fiber pigtail 268 via the combiner 200 and lens 264.

As described previously, there are a number of potential implementations of the combiner stage 200. In one example, the combiner 200 combines the light from the tunable lasers using a WDM filter. In this implementation, a first spectral scan band of first tunable laser 100-1 and the second spectral scan band of second tunable laser 100-2 are non-overlapping spectral scan bands. The fold mirror 254 directs the light to a beam combining element 252, which is a WDM filter that reflects light in the second spectral scan band and transmits light in the first spectral scan band.

In another example, the first tunable optical signal 128-1 and the second tunable optical signal 128-2 have orthogonal polarizations. A quarter wave plate 262 is used to rotate the polarization of the second tunable optical signal 128-2 from the second tunable laser 100-2 if required. In other examples, the SOA chips produce optical signals of orthogonal polarizations. The signals are combined in the combined optical signal 256 using a polarization beam combiner as the beam combining element 252. Since this example relies on polarization diversity, it works when the first spectral scan band and the second spectral scan band the same, overlapping, contiguous, and non-overlapping.

In still another example, the first tunable optical signal 128-1 and the second tunable optical signal 128-2 are time multiplexed. Here, the light from the two cavities is combined using a beam switch, in one implementation, as the beam combining element 252 by alternately passing either the first tunable optical signal 128-1 or the second tunable optical signal 128-2 as the combined signal 256.

In still another example, the beam combining element 252 is a 50/50 beamsplitter/combiner. In this example, however, the beam splitter 252 is an intra-cavity element. Thus, the loss associated with the element is higher than in the previous embodiments.

One advantage of using the shared reflector 270 along with the fiber pigtail 268 is that it enables greater latitude in adjusting the lengths of the optical cavities of the tunable laser swept sources 100-1, 100-2. Generally, shorter laser cavities translate to higher potential tuning speeds. The round-trip travel time for the light in the laser cavities is kept low so that lasers can tune at very high speed. Short laser cavities, however, create problems in terms of the spacing of the longitudinal cavity modes. That is, lasers can only produce light at integer multiples of the cavity length since the light must oscillate within the cavities. Shorter cavities result in fewer and more widely spaced modes. Fewer cavity modes result in greater mode hopping noise as the laser is tuned over these cavity modes.

In the current embodiment, the optical length of each of the laser cavities for the tunable laser swept sources 100-1, 100-2 is adjustable by controlling the length of the fiber pigtail 268. In the current embodiment, the fiber pigtail is between 3 and 9 centimeters, preferably 60 millimeters (mm), long for lasers generating light with a center wavelengths of 1310 and 1060 nanometers in length. This results in a good trade-off between the tuning speed of the tunable laser swept sources 100-1, 100-2 while yielding acceptable mode hopping noise as the lasers are tuned over the their spectral scan bands.

In the preferred embodiment, an intracavity birefringence control element 565 is further provided. This element further functions as a splicing device that couples the pigtail 270 to optical fiber 320.

Typically, the SOA has gain in only one preferential polarization direction. As described previously, light reflected from the fiber mirror coating 270 in the control element 565 serves as one mirror of the laser cavities. However, single-mode fiber (non polarization-maintaining), which is often preferred for OCT applications. Polarization maintaining (PM) fiber can cause ghost images due to some light coupling into the undesired fiber axis and experiencing a longer time delay. Single mode fiber, however can arbitrarily rotate the polarization state of the light (called birefringence) and thus degrade laser feedback over the tuning range. Further, stress from soldering the fiber to the bench B or to any fiber feed through 502 in package 500 further induces birefringence. In the worst-case instance, it can prevent lasing if the reflected light's direction of polarization ends up orthogonal to the preferred polarization state of the SOAs 410-1, 410-2.

Inserting a birefringence control element 565 in the laser cavities of tunable laser swept sources 100-1, 100-2 compensates by properly aligning the polarization state of the reflected light.

Figure 8:
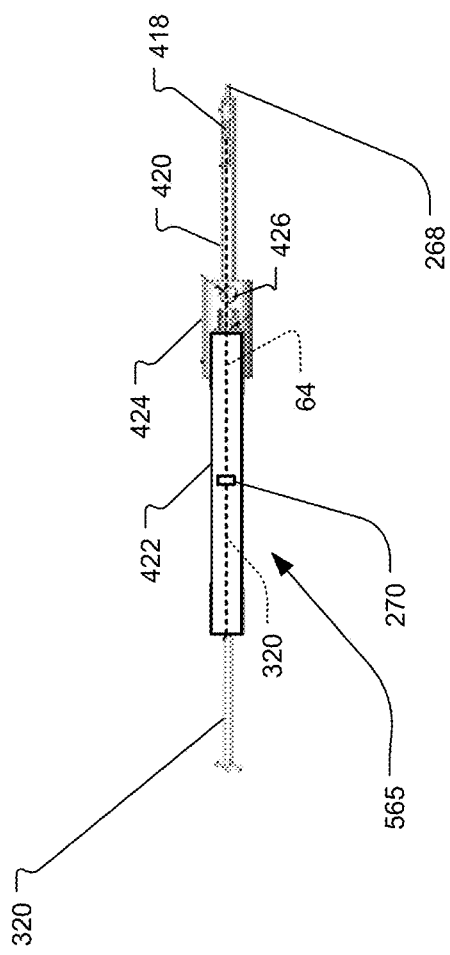
FIG. 8 is a diagram of a birefringence controller used in the swept source optical system.

FIG. 8 shows one implementation of the birefringence control element 565 that can provide a relatively short fiber cavity (from 3 to 8 cm) and allows for polarization alignment and fiber stability in a compact fixture, which is a mechanical fiber splicing device.

The fiber stub 268 is held by two points in the mechanical fiber splicing device. 1) solder at point 418 that connects fiber 268 to tube 420, which is the coupler's ferrule; and 2) by the mechanical splice between fiber 268 and fiber 320 at the optical coating/combined reflector 270.

One commercially available example of mechanical fiber splicing device is the 3M™ Fibrlok™ II Universal Optical Fiber Splice, which is mechanical splice device that allows the coupling the reflective (HR) coated fiber 270 to the output fiber 320. In other examples, a fusion splice with an HR coating is used to couple fiber 268 to fiber 320.

This mechanical splice is fixed within the body 422 typically by an epoxy bond. A cylindrical holder 424 is fixed to the body 422 and has an inner bore into which the tube 420 is inserted. A set screw 426 enables the tube 420 to be rotated relative to the cylindrical holder 424 and then be fixed to the holder 424 when the set screw 426 is tightened down. This allows a mechanical stress to be imparted to fiber 268 in its length between solder 418 and the region of the shared reflector 270 that is secured to body 422. This stress affects the birefringence of the fiber 268 and thus affects the polarization state of the light within the laser cavities of the tunable laser swept sources 100-1, 100-2.

In operation and typically in a manufacturing/calibration stage, with the set screw 426 loosened, an operator twists the fiber 268 by rotating the body 422 about the stainless steel tube 420. The output of the dual swept source 100 is monitored by a detector connected to a high speed oscilloscope. Twisting of the fiber stub 268 induces polarization changes. When optimal operation is observed, characterized by a maximum power output from the lasers and smooth tuning, i.e., reduced changes in power as a function of frequency during tuning and the change in frequency as a function of time is linear or near linear during tuning, over the desired tuning range without any polarization fading, the set screw 426 is tightened to fix the stress applied to the fiber 268. The stainless steel tube 420 prevents any subsequent fiber movement and thus maintains polarization stability. In this way, the mechanical fiber splicing device functions as a birefringence control element 565 that is used to compensate for other birefringence. This enables polarization matching to occur over the whole wavelength tuning range of the dual swept source 100 with any residual birefringence of the SMF fiber being small.

Figure 9:
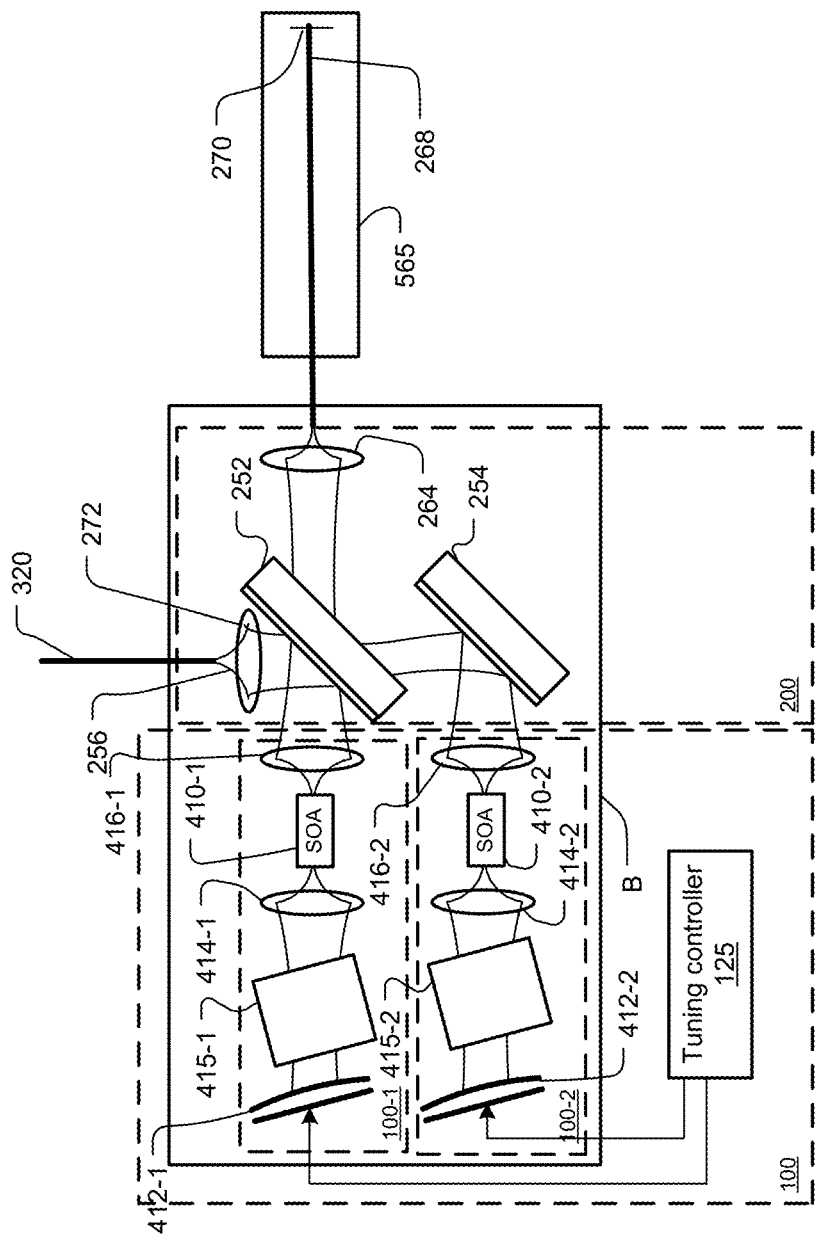
FIG. 9 is a schematic diagram of a dual laser swept optical source with a shared optical cavity according to another embodiment.

FIG. 9 shows another embodiment of the dual swept optical source 100, using laser sources, according to the principles of the present invention.

It is similar to the embodiment shown in FIG. 7. It incorporates the birefringence control element 565 and the fiber pigtail 268 that forms a portion of the shared optical cavity for the tunable laser swept sources 100-1, 100-2. In this embodiment, the shared reflector 270 is preferably a 100% reflecting mirror. Light is instead extracted from the tunable laser swept sources 100-1, 100-2 via the combiner 200.

In more detail, the combining element 252 in this embodiment is a beam splitter. As a result, a portion of the light from both of the tunable laser swept sources 100-1, 100-2 is transmitted to the shared reflector 270. The light that is not reflected by the beam splitter 252 from the second tunable laser swept source 100-2 and the light that is reflected by the beam splitter 252 from the first tunable laser swept source 100-1 is collimated by output lens 272 and coupled into output optical fiber 320 for transmission to the OCT interferometer.

Figure 10:
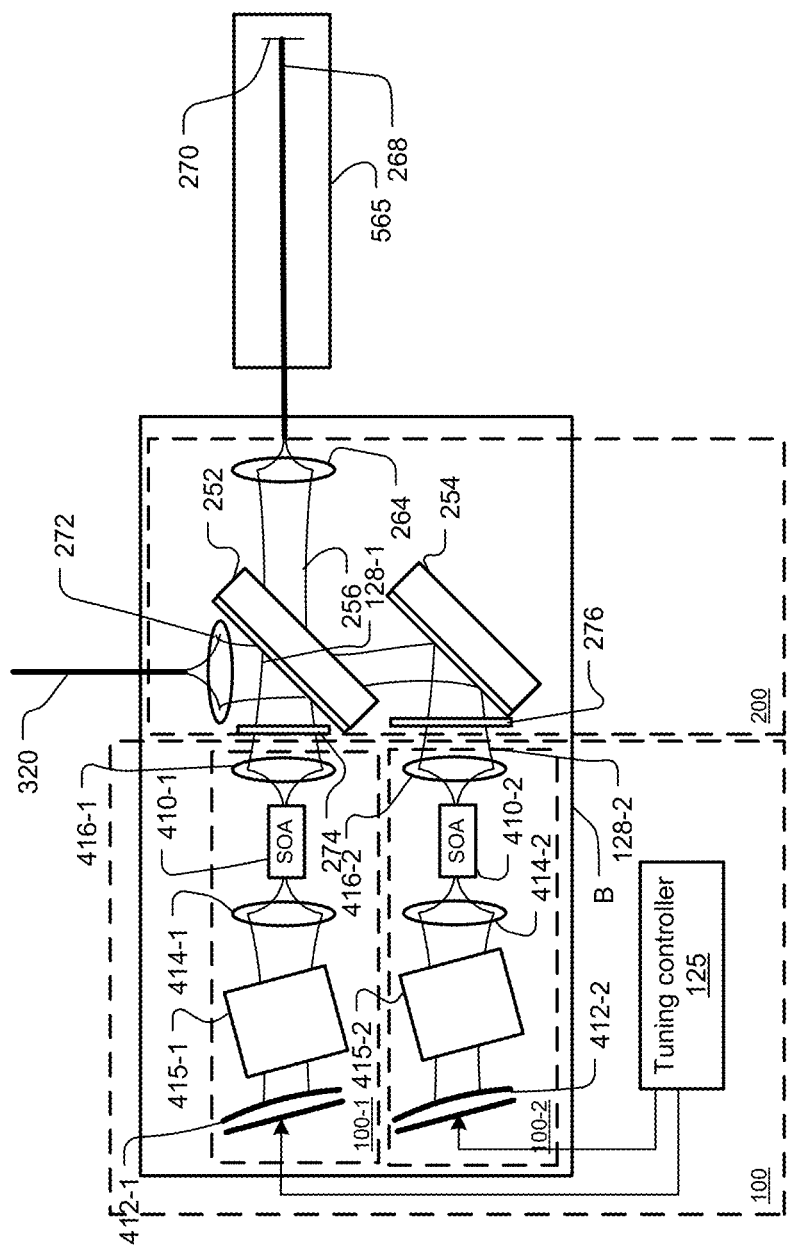
FIG. 10 is a schematic diagram of a dual laser swept optical source with a shared optical cavity according to still another embodiment.

FIG. 10 shows another embodiment of the dual swept optical source 100, using laser sources, according to the principles of the present invention.

This embodiment is similar to the embodiment discussed with respect to FIG. 9. It differs in that the combining element 252 is a polarization beam splitter. Further, two adjustable quarter wave plates are added in the laser cavities of the tunable laser swept sources 100-1, 100-2. These adjustable quarter wave plates 274, 276 are located between the combiner 200 and the SOAs 410-1, 410-1.

During manufacture, the adjustable quarter wave plates 274, 276, are rotated to adjust the polarization of the light transmitted to the combiner 252. Changing their polarizations changes the degree to which they are reflected or transmitted by the polarization beam splitter element 252. This has the effect of providing control over the light that is coupled from the optical cavities of the tunable laser swept sources 100-1, 100-2 to output lens 272 and into the optical fiber 320 that transmits the combined tunable optical signal to the OCT interferometer.

In the preferred embodiment, the adjustable quarter wave plates 274, 276 are adjusted such that approximately 50-99 percent of the light is coupled out of the respective optical cavities and into the optical fiber 320.

Figure 11:
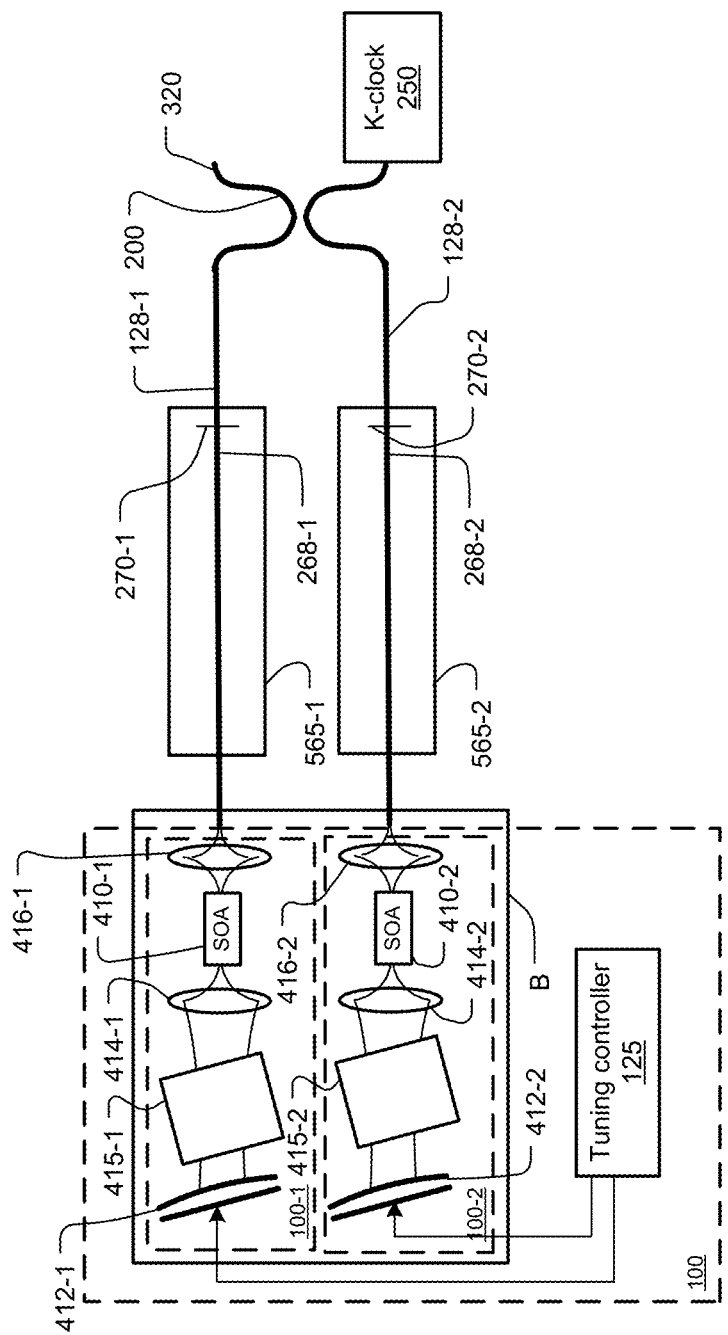
FIG. 11 is a schematic diagram of a dual laser swept optical source with according to still another embodiment with birefringence controllers for each individual swept source.

FIG. 11 shows another embodiment of the dual swept optical source 100, using laser sources, according to the principles of the present invention.

This embodiment differs from some of the previous embodiments in that it has no shared optical cavities between the two tunable laser swept sources 100-1, 100-2.

Separate lenses 416-1, 416-2 couple light from the laser cavities into separate fiber pigtails 268-1, 268-2 to separate birefringence compensators 565-1, 565-2 and separate with partial reflectors 270-1, 270-2. The first tunable optical signal 128-1 and the second tunable optical signal 128-2 are combined in a fiber coupler that functions as the combiner 200. One of the output ports of this combiner 200 is then coupled to the optical fiber 320 that transmits the combined optical signal to the OCT interferometer. Preferably, the other port of the combiner 200 is coupled to the k-clock 250.

This embodiment has the advantage that the separate birefringence compensators 565-1, 565-2 are individually adjustable in order to compensate for birefringence for each of the tunable laser swept sources 100-1, 100-2 separately. Further, the use of the separate optical cavities and in particular the separate fiber pigtails 268-1, 268-2 allows for the individual adjustment of the cavity lengths of the tunable laser swept sources 100-1, 100-2.

Figure 12:
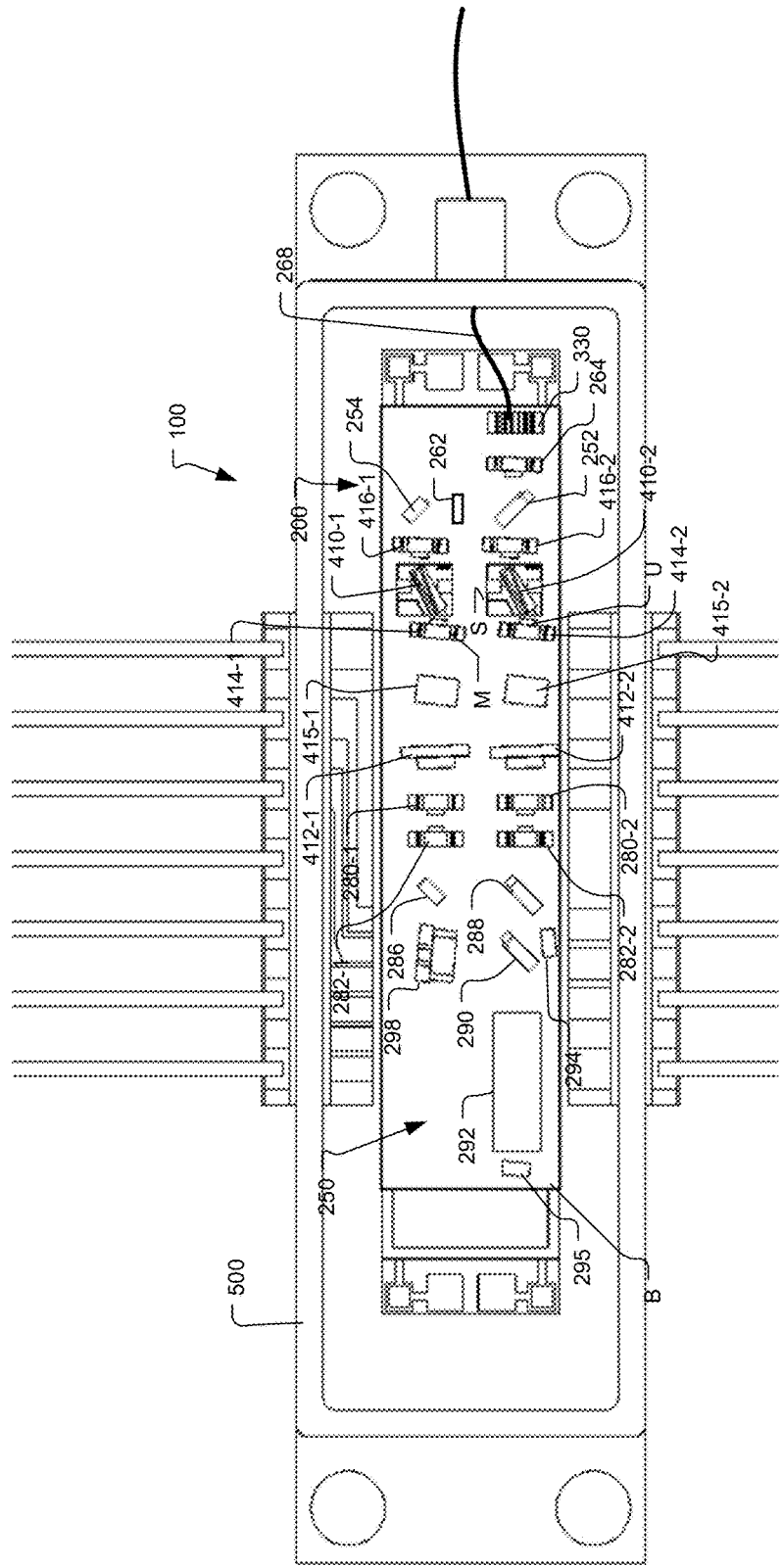
FIG. 12 is a top plan scale drawing of the dual laser swept optical source.

FIG. 12 shows another embodiment of the dual swept optical source 100, using laser sources, and including an integrated laser clock system 250 that has been constructed according to the principles of the present invention.

Generally the integrated dual laser clock system 100 comprises a two tunable laser subsystems, which generates a wavelength or frequency tunable first and second optical signals, and a clock subsystem 250, which generates clock signals at equally spaced frequency increments as the tunable signals or emissions of the laser 100 are spectrally tuned over a spectral scan band(s). The clock signals are used to trigger sampling of the analog to digital converter subsystem 315.

The tunable dual laser subsystem 100, combiner 200, and clock subsystem 250 of the integrated laser system 100 are integrated together on a common optical bench B. This bench B is termed a micro-optical bench and is preferably less than 20 millimeters (mm) by 30-50 mm in size so that it fits within a standard or near standard butterfly or DIP (dual inline pin) hermetic package 500. In one implementation, the bench B is fabricated from aluminum nitride. A thermoelectric cooler is disposed between the bench B and the package 500 (attached/solder bonded both to the backside of the bench B and inner bottom panel of the package 500) to control the temperature of the bench B.

In the current implementation, the tunable lasers each comprise semiconductor gain chip 410-1, 410-2 that is paired with a micro-electro-mechanical (MEMS) angled reflective Fabry-Perot tunable filters 412-1, 412-2 to create external cavity laser (ECL) with the tunable filters being an intracavity tuning element and forming one end, or back reflector, of laser cavities.

The semiconductor optical amplifier (SOA) chips 410-1, 410-2 are located within their respective laser cavities. In the current embodiment, both facets of the SOA chip 410-1, 410-2 are angled relative to a ridge waveguide. The SOA chips 410 are mounted on submounts S that, in turn, are mounted on the top side of the optical bench B, typically by solder bonding.

To collect and collimate the light exiting from each end facet of the SOAs 410-1, 410-2, lens structures 414-1, 414-2 and 416-1, 416-2 are used. Each lens structure comprises a LIGA mounting structure M, which is deformable to enable post installation alignment, and a transmissive substrate U on which the lens is formed. The transmissive substrate U is typically solder or thermocompression bonded to the mounting structure M, which in turn is solder bonded to the optical bench B.

The first lens components 414-1, 414-2 couple the light between the input facet of the SOAs 410-1, 410-2 and the tunable filters 412-1, 412-2. Light exiting out the output facets of the SOAs 410-1, 410-2 are coupled by lens component 416-1, 416-2 to optical fiber 320 via its front facet. The optical fiber pigtail 268 that leads to the birefringence compensator and external cavity reflector 270 is also preferably solder attached to the optical bench B via a mounting structure 330.

In more detail, fold mirror 254 directs the second optical signal to combiner 252, which is configured according to one of the previous described options, through a halfwave plate 262, if required. The combined beam is then coupled into optical fiber 268 by lens 261 to the optical fiber facet that is held by mounting structure 330.

The light transmitted by the tunable filters 412-1, 412-2 is coupled out of the laser cavities and into the clock subsystem 250 to be collimated by a third lens component 280-1, 280-2 and fourth lens components 282-1, 282-2 for each tunable laser, which are solder bonded to the optical bench B.

Fold mirror 286 and beam combiner 288 combine the beams from each tunable laser into a common beam. The light then passes through a beam splitter 290, which is preferably a 50/50 splitter to a clock etalon 292. Any light reflected by the splitter 290 is directed to a beam dump component 294 that absorbs the light and prevents parasitic reflections in the hermetic package 500 and into the laser cavities.

The clock etalon 292 functions as a spectral filter. Its spectral features are periodic in frequency and spaced spectrally by a frequency increment related to the length and refractive index of the constituent material of the clock etalon 292, which is fused silica in one example. The physical length of etalon 292 is L. The etalon can alternatively be made of other high-index and transmissive materials such as silicon for compactness, but the optical dispersion of the material may need to be compensated for with additional processing inside the DSP. Also, air-gap etalons, which are nearly dispersionless, are another alternative. Still a further alternative is a free-space interferometer (e.g. a Michelson), which also is dispersionless and is adjusted by simply moving the relative positions of the mirrors.

The contrast of the spectral features of the etalon is determined by the reflectivity of its opposed endfaces. In one example, reflectivity at the etalon endfaces is provided by the index of refraction discontinuity between the constituent material of the etalon and the surrounding gas or vacuum. In other examples, the opposed endfaces are coated with metal or preferably dielectric stack mirrors to provide higher reflectivity and thus contrast to the periodic spectral features.

In the illustrated example, the clock etalon 292 is operated in reflection. The light returning from the clock etalon 292 and reflected by beamsplitter 290 is detected by detector 298. The light detected by detector 298 is characterized by drops and rises in power as the frequency of the tunable signal scans through the reflective troughs/reflective peaks provided by the clock etalon 298. Light transmitted by the etalon 292 is collected by beam dump 295.

Figure 13:
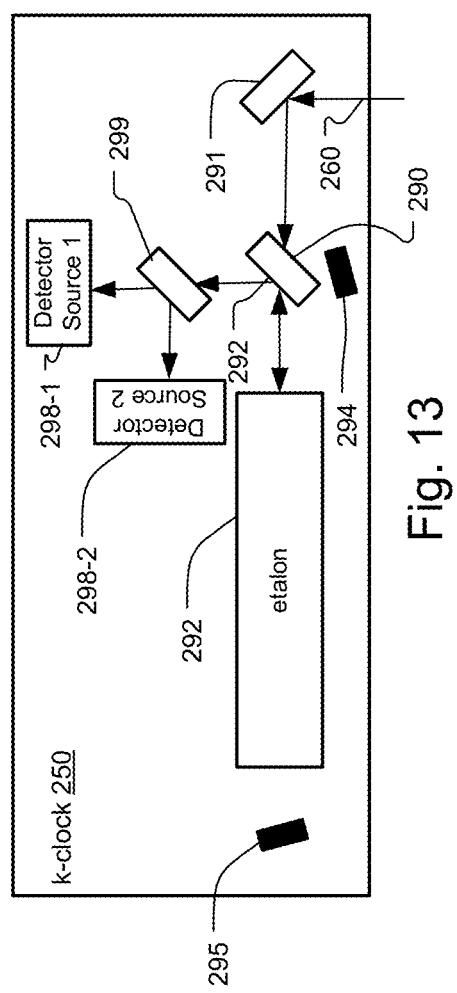
FIG. 13 is a top plan view of a multichannel k-clock system according to the present invention.

FIG. 13 shows another implementation of the k-clock 250 that allows for the simultaneous monitoring of both the first tunable optical signal and the second tunable optical signal from the swept sources.

In more detail, input beam 260 from the beam combiner 200 is reflected by a fold mirror 291. The light then passes through a beam splitter 290, which is preferably a 50/50 splitter to a clock etalon 292. Any light reflected by the splitter 290 is directed to a beam dump component 294 that absorbs the light and prevents parasitic reflections in the hermetic package 500 and into the laser cavities.

As described previously, the clock etalon 292 functions as a spectral filter. Its spectral features are periodic in frequency and spaced spectrally by a frequency increment related to the length and refractive index of the constituent material of the clock etalon 292, which is fused silica in one example.

In the illustrated example, the clock etalon 292 is operated in reflection. The light returning from the clock etalon 292 and reflected by beamsplitter 290 is received by a splitter element 299. In a situation where are the first tunable optical signal and the second tunable optical signal operate in different spectral scan bands, the splitter element is a WDM filter that transmits the light associated with the first tunable optical signal to a first detector 298-1 and reflects light associated with the second tunable optical signal to a second detector 298-2. In this way, the detectors 298-1, 298-2 are used to generate separate k-clock signals simultaneously for each of the first tunable optical signal and the second tunable optical signal.

FIG. 14A illustrates the scanning of a conventional swept source. The source sequentially a tunes through the wavelength scan band S. This is the repeated in serial scans. The problem is that the scans cannot be performed in close time spacing without going to an different system configuration such as ring laser cavities with polygon filters. Instead there is a gap between successive scans S associated with the retrace period R. While it is possible to scan in both directions, this is typically not feasible since semiconductor gain elements preferably only scan in one direction due to the Bogatov effect. In addition, the mechanical inertia of the MEMS filter prevents a quick resweep at high tuning speeds.

FIG. 14B illustrates the scanning of dual swept source according to one example under control of the tuning controller 125. Here, a first of optical signal is scanned as illustrated by scan S1. Then, a second tunable optical signal is scanned as illustrated scan S2. The process is then repeated for subsequent scans. In this embodiment, the scans for each of the two of optical signals occur over the same wavelength scan bands. The duty cycle is in effect doubled. In this example, a combiner 200 that implements a beam switch can be used due to the time multiplexed nature of the tunable optical signal scans S1, S2. Alternatively, the first swept source and the second swept source are alternately energized such that only one is emitting at any given time. As such, a partially reflecting element or mirror is used as the combining element 252, in the simplest implementation.

This scanning configuration also enables speckle averaging with two consecutive A-lines (polarization diversity or not). The speckle pattern is different for different scan times of biological samples.

FIG. 14C illustrates the scanning of the dual swept source according to still another example. Here each of the scans S1, S2 have different polarizations as indicated by the inset arrows. Thus while in this example a beam switch combiner 200 could be used, in the preferred embodiment, the combiner 200 utilizes a polarization beam combiner.

FIG. 14D illustrates still another example in which these successive scans S1, S2 associated with the first tunable optical signal and the second tunable optical signal occur over contiguous scan bands. Specifically scan S1 occurs at a shorter wavelengths whereas scan S2 occurs over a range of longer wavelengths.

FIG. 14E illustrates still another example in which these successive scans S1, S2 associated with the first tunable optical signal and the second tunable optical signal occur over non-overlapping scan bands. Specifically scan S1 occurs at a shorter wavelengths whereas scan S2 occurs over a range of longer wavelengths that are separated from the scan band of S1 by a guard band. G.

Figure 14F:
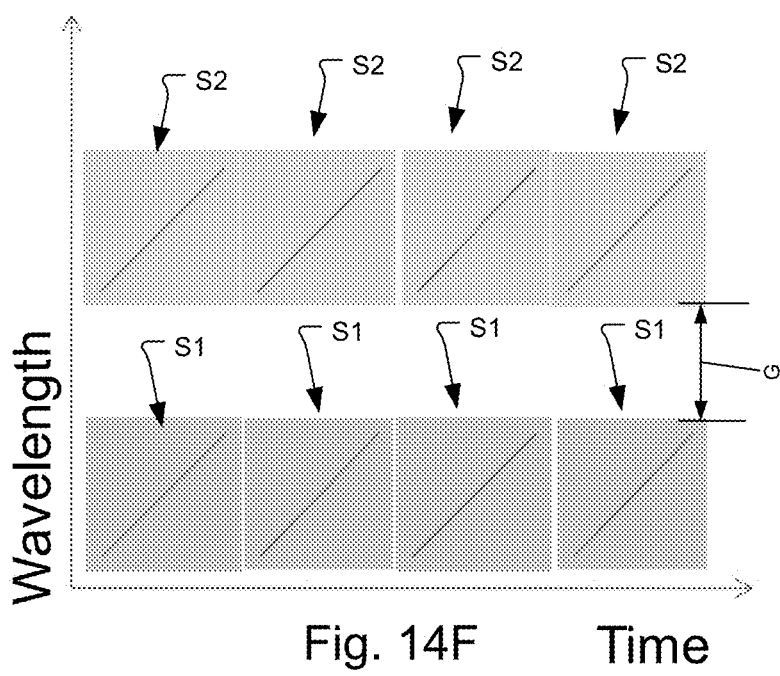

FIG. 14F illustrates still another example in which these successive scans S1, S2 associated with the first tunable optical signal and the second tunable optical signal occur over non-overlapping scan bands, and simultaneously in time. Specifically scan S1 occurs at shorter wavelengths whereas scan S2 occurs over a range of longer wavelengths that are separated from the scan band of S1 by a guard band. G. The scans occur simultaneously with each other using a combination of a WDM combiner 200 and WDM separation at detection.

Figure 15:
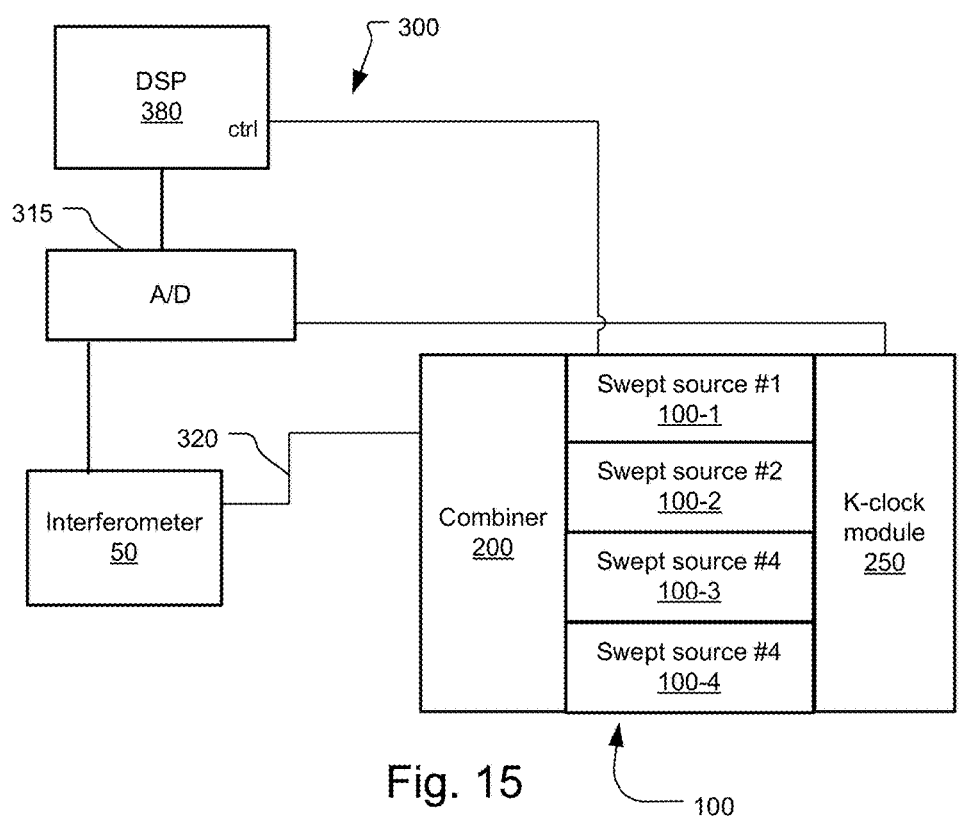
FIG. 15 is a block diagram showing an OCT system with a four swept sources.

FIG. 15 shows an optical coherence analysis system 300 using the integrated multiple swept source system 100, which has been constructed according to the principles of the present invention.

The previous examples focused on dual swept source systems. However, in alternative examples, more than two swept sources are included in the integrated swept source system 100. This embodiment illustrates a source system 100 with four swept sources: a first swept source 100-1, a second swept source 100-2, a third swept source 100-3, and a fourth swept source 100-4. Each of these individual swept sources generates respective tunable optical signals, a first optical signal, a second optical signal, a third optical signal, a fourth optical signal, which are combined into the combined optical signal by a combiner 200 and coupled onto the optical fiber 320.

Using four sources has the advantages of higher speed, higher resolution, and 100% duty cycle when using a two detectors system set up as shown in FIG. 2, one for each band. Further, higher speed and polarization sensitivity with four sources using two sources with one polarization and two with another is possibility.

Figure 16A:
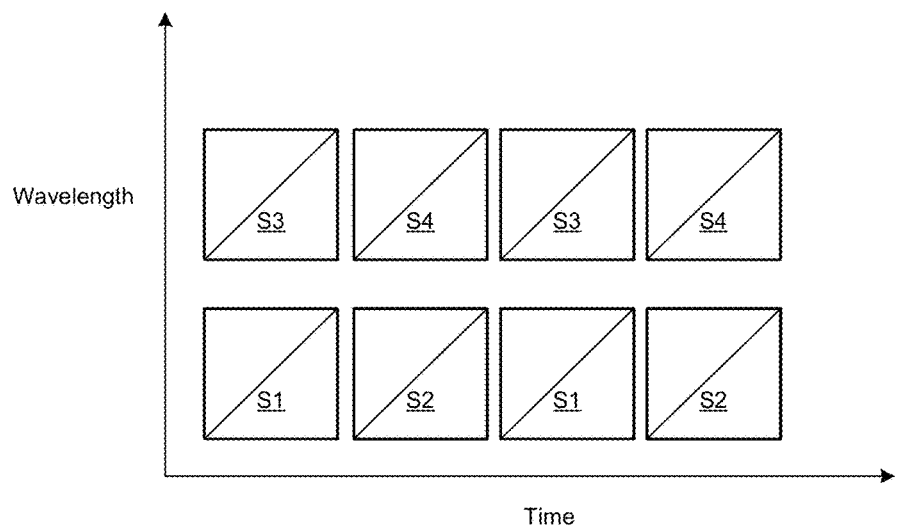
FIGS. 16A and 16B are plots of wavelength as a function of time showing swept source scanning, simultaneously over two and four different scan bands, respectively.

FIG. 16A illustrates the scans S1, S2, S3, S4 associated with the first tunable optical signal, the second tunable optical signal, the third tunable optical signal, the fourth tunable optical signals generated by a first swept source 100-1, a second swept source 100-2, a third swept source 100-3, and a fourth swept source 100-4, respectively. In this example, the scans S1, S2 take place over a first scan band with 100%, or near 100% duty cycle. Likewise scans S3, S4 take place over a second scan band with 100%, or near 100% duty cycle.

Figure 16B:
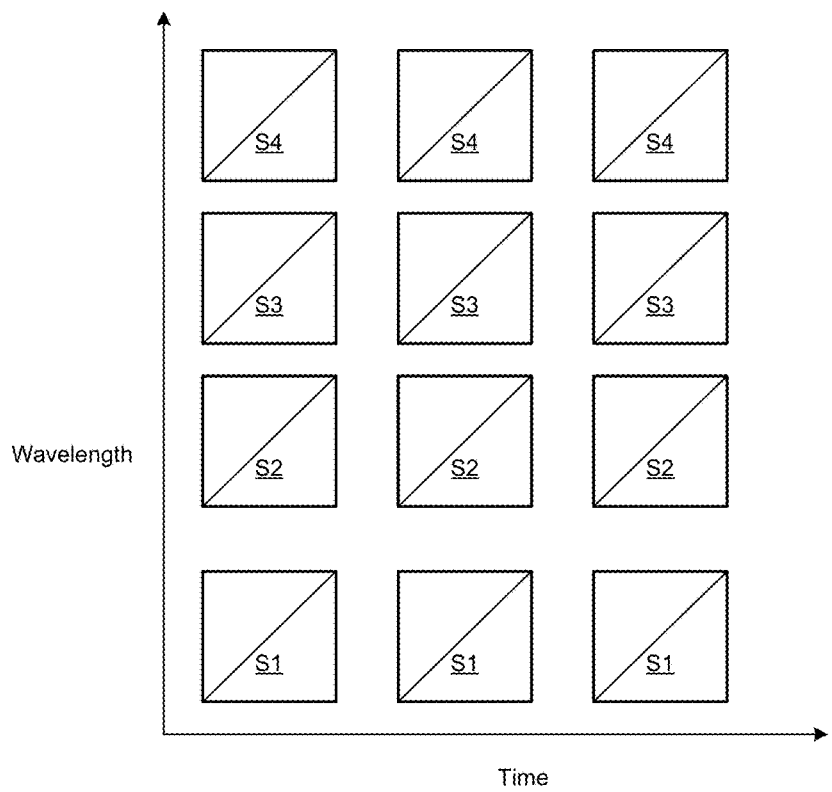

FIG. 16B illustrates the successive scans S1, S2, S3, S4 associated with the first tunable optical signal, the second tunable optical signal, the third tunable optical signal, the fourth tunable optical signals generated by a first swept source 100-1, a second swept source 100-2, a third swept source 100-3, and a fourth swept source 100-4, respectively. In this example, the scans S1, S2, S3, S4 occur over non-overlapping scan bands, and simultaneously in time.

Figure 17:
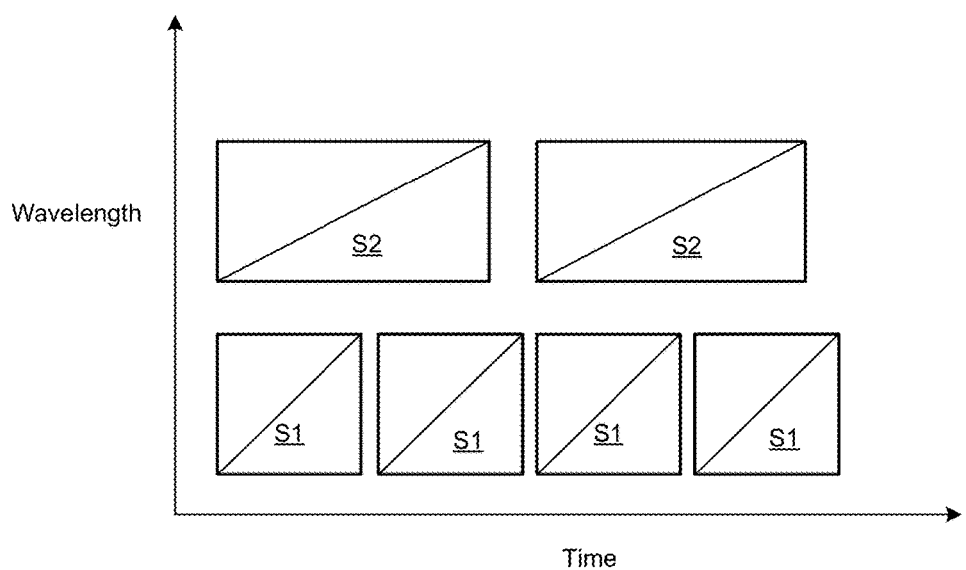
FIG. 17 is plot of wavelength as a function of time showing swept source scanning, simultaneously over two different scan bands with different scan rates.

FIG. 17 illustrates an alternative scanning regime. Here the S1 scans from the first optical signal is at a higher scan rate than the scans S2 of the second tunable optical signal. In particular, the scans S1 associated with the first tunable optical signal are relatively fast, twice as fast in the illustration, than the spectral scans of the second tunable optical signal S2. This embodiment is useful when different pathlengths are being investigated by the separate tunable optical signals in the sample. In other examples, the slower scan is associated with the spectral analysis of the sample where is the higher rate scan is associated with the OCT analysis of the sample. This dual modality analysis is used for example in the hybrid spectral/OCT analysis system of FIG. 3.

While this invention has been particularly shown and described with references to preferred embodiments thereof, it will be understood by those skilled in the art that various changes in form and details may be made therein without departing from the scope of the invention encompassed by the appended claims. For example, although the invention has been described in connection with an OCT or spectroscopic analysis, the invention could also be applied along with IVUS, FLIVUS, HIFU, pressure sensing wires and image guided therapeutic devices.

What is claimed is:

1. An optical coherence analysis system comprising:
   a first swept source that generates a first optical signal that is tuned over a first spectral scan band, the first swept source including a first semiconductor optical amplifier and a first tunable filter for tuning light from the first semiconductor amplifier over the first spectral scan band;
   a second swept source that generates a second optical signal that is tuned over a second spectral scan band, the second swept source including a second semiconductor optical amplifier and a second tunable filter for tuning light from the second semiconductor amplifier over the second spectral scan band;
   a combiner for combining the first optical signal and the second optical signal to form a combined optical signal;
   an interferometer for dividing the combined optical signal between a reference arm leading to a reference reflector and a sample arm leading to a sample;
   a multi channel k-clock system for detecting the first optical signal and the second optical signal to generate clock signals, wherein the multi channel k-clock system receives the combined optical signal and separately detects the first optical signal with a first detector to generate a first clock and the second optical signal with a second detector to generate a second clock as the clock signals;
   a detector system for detecting an interference signal generated from the combined optical signal from the reference arm and from the sample arm; and
   an analog to digital converter system that samples the interference signal and also receives the clock signals.

2. A system as claimed in claim 1, wherein the combined optical signal is coupled into a spectrally filtering element.

3. A system as claimed in claim 2, wherein the spectrally filtering element is an etalon.

4. A system as claimed in claim 1, further comprising an optical bench, on which the first swept source, second swept source and the multi channel k-clock system are implemented.

5. A system as claimed in claim 1, wherein the multi channel k-clock system comprises a beam splitter for dividing the first optical signal from the second optical signal and providing the first optical signal to the first detector and the second optical signal to the second detector, respectively.

6. A system as claimed in claim 5, wherein the beam splitter is a WDM filter.

7. An optical coherence analysis method comprising:
generating a first optical signal that is tuned over a first spectral scan band with a first swept source including a first semiconductor optical amplifier and a first tunable filter for tuning light from the first semiconductor amplifier over the first spectral scan band, wherein components of the first swept source are attached to an optical bench;
generating a second optical signal that is tuned over a second spectral scan band with a second swept source including a second semiconductor optical amplifier and a second tunable filter for tuning light from the second semiconductor amplifier over the second spectral scan band, wherein components of the second swept source are attached to the optical bench;
combining the first optical signal and the second optical signal to form a combined optical signal;
dividing the combined optical signal between a reference arm leading to a reference reflector and a sample arm leading to a sample;
detecting the first optical signal and the second optical signal to generate clock signals by receiving the combined optical signal and then separately detecting the first optical signal to generate a first clock with a first detector and the second optical signal to generate a second clock with a second detector; and
processing an interference signal generated from the combined optical signal from the reference arm and from the sample arm in response to the clock signals.

8. A method as claimed in claim 7, wherein the combined optical signal is coupled into a spectrally filtering element.

9. A method as claimed in claim 8, wherein the spectrally filtering element is an etalon.

10. A method as claimed in claim 7, further comprising generating the first optical signals, the second optical signals, and the clock signals on an optical bench.

11. A method as claimed in claim 7, further comprising dividing the first optical signal from the second optical signal prior to detection by the separate detectors.

12. A method as claimed in claim 11, further comprising the first optical signal from the second optical signal with a WDM filter.

13. A system as claimed in claim 1, wherein the multi channel k-clock is attached to the optical bench.

14. A method as claimed in claim 7, wherein the clock signals are generated by a k-clock system that is attached to the optical bench.

* * * * *